United States Patent
Petillo et al.

(10) Patent No.: US 9,468,402 B2
(45) Date of Patent: Oct. 18, 2016

(54) TISSUE IMPLANTABLE MICROBIOSENSOR

(75) Inventors: Peter A. Petillo, Lawrence, KS (US);
George S. Wilson, Lawrence, KS (US);
Judy Z. Wu, Lawrence, KS (US);
Mark L. Richter, Lecompton, KS (US); David A. Johnson, Lawrence, KS (US); Daniel V. Aillon, Lawrence, KS (US)

(73) Assignee: Pinnacle Technology, Inc., Lawrence, KS (US)

( * ) Notice: Subject to any disclaimer, the term of this patent is extended or adjusted under 35 U.S.C. 154(b) by 706 days.

(21) Appl. No.: 13/991,113

(22) PCT Filed: Dec. 1, 2011

(86) PCT No.: PCT/US2011/062951
§ 371 (c)(1),
(2), (4) Date: Aug. 12, 2013

(87) PCT Pub. No.: WO2012/075331
PCT Pub. Date: Jun. 7, 2012

(65) Prior Publication Data
US 2013/0324820 A1    Dec. 5, 2013

Related U.S. Application Data

(60) Provisional application No. 61/418,642, filed on Dec. 1, 2010.

(51) Int. Cl.
*A61B 5/05* (2006.01)
*A61B 5/1486* (2006.01)
*A61B 5/145* (2006.01)
*C25D 7/00* (2006.01)

(52) U.S. Cl.
CPC ....... *A61B 5/14865* (2013.01); *A61B 5/14532* (2013.01); *C25D 7/00* (2013.01); *A61B 2562/12* (2013.01)

(58) Field of Classification Search
CPC .................................................. A61B 5/14532
See application file for complete search history.

(56) References Cited

U.S. PATENT DOCUMENTS

| 4,919,141 A | 4/1990 | Zier et al. |
| 6,233,471 B1 | 5/2001 | Berner et al. |
| 6,802,957 B2 | 10/2004 | Jung et al. |
| 6,814,845 B2 | 11/2004 | Wilson et al. |
| 7,076,987 B2 | 7/2006 | Martin et al. |

(Continued)

FOREIGN PATENT DOCUMENTS

WO    2010/040648    4/2010

OTHER PUBLICATIONS

Feng et al., "Electrochemical Pretreatment of Carbon Fibers for in Vivo Electrochemistry: Effects on Sensitivity and Response Time," Anal. Chem., Jul. 15, 1987, vol. 59, No. 14, 1863-1867.

(Continued)

*Primary Examiner* — Christian Jang
(74) *Attorney, Agent, or Firm* — Hovey Williams LLP

(57) ABSTRACT

A biosensor system comprises a capillary substrate, conductive electrode, and a plurality of nanoparticles having an enzyme deposited thereon formed in a cavity at one end of the capillary substrate. The substrate may have an optional reinforcing layer (which may be conductive or non-conductive) and optional insulating layer thereon. A cannula having an optional conductive layer, insulating layer, and reference electrode may also form part of the system.

30 Claims, 21 Drawing Sheets

(56) References Cited

U.S. PATENT DOCUMENTS

Figure 1A:
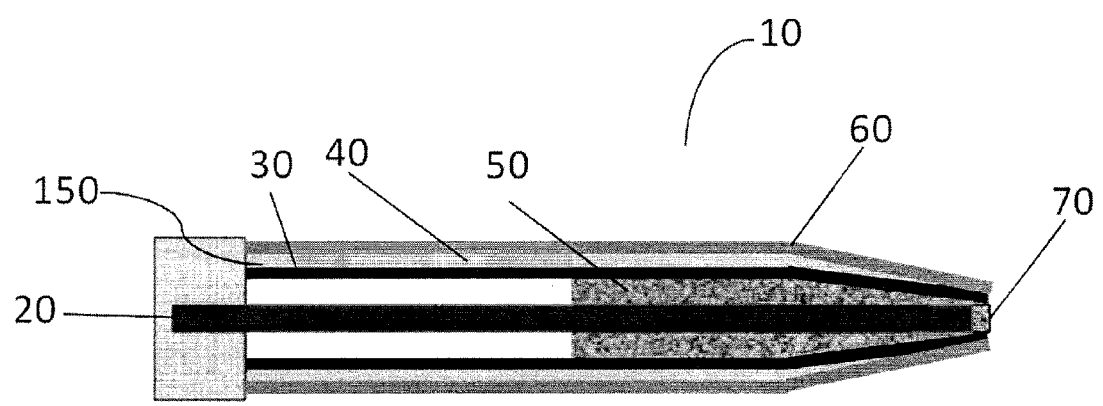

| | | | |
|---|---|---|---|
| 7,310,543 B2* | 12/2007 | Smart ............... | A61B 5/14532 600/345 |
| 8,771,500 B2* | 7/2014 | Papadimitrakopoulos | C01B 13/0248 204/403.01 |
| 2003/0032892 A1 | 2/2003 | Erlach et al. | |

OTHER PUBLICATIONS

Jung et al., "Oxygen Microsensor and Its Application to Single Cells and Mouse Pancreatic Islets," Anal. Chem., Sep. 1, 1999, vol. 71, No. 17, 3642-3649.

Jung et al., "Development and Application of a Self-Referencing Glucose Microsensor for the Measurement of Glucose Consumption by Pancreatic β-Cells," Anal. Chem., Aug. 1, 2001, vol. 73, No. 15, 3759-3767.

Yu et al., "Large-area blown bubble films of aligned nanowires and carbon nanotubes," Nature Nanotechnology, Jun. 2007, vol. 2, 372-377.

Dizon et al., "Improved near-field scanning microwave microscope combined with electrical transport measurement for characterizing nonuniformity of electrical dissipation in Y Ba 2 Cu 3 O 7-δ films of variable thickness," Journal of Applied Physics, 2010, vol. 107, 043905.

Ammam et al., "Micro-biofuel cell powered by glucose/O2 based on electro-deposition of enzyme, conducting polymer and redox mediators: Preparation, characterization and performance in human serum," Biosensors and Bioelectronics 25, 2010, 1474-1480.

Ammam et al., "AC-electrophoretic deposition of glucose oxidase," Biosensors and Bioelectronics 25, 2009, 191-197.

Ammam et al., "A study on electrodeposition of glucose oxidase from low conductivity solutions," Electrochimica Acta 55(28), 2010, 9125-9131.

Lindahl et al, "Glycosaminoglycans and Their Binding to Biological Macromolecules," Ann. Rev. Biochem., 1978, 47:385-417.

Hassell et al., "Proteoglycan Core Protein Families," Ann. Rev. Biochem., 1986, 55:539-567.

Yeung et al., "Synthesis of Glycosaminoglycans," Glycochemistry: Principles, Synthesis and Applications, Bertozzi, C.R. and Wang, P.G., Eds., Marcel Dekker, Inc. 2001, Chapter 12, pp. 425-492.

Yeung et al., "Synthesis of Glycosaminoglycans," Journal of Carbohydrate Chemistry, 2002, vol. 21, Nos. 7-9, pp. 799-865.

Pyell, Ute, "Characterization of nanoparticles by capillary electromigration separation techniques," Electrophoresis, 2010, 31(5), 814-831.

Tantra et al., "Effect of nanoparticle concentration on zeta-potential measurement results and reproducibility," Particuology 8(3), 2010, 279-285.

Yu et al., "An independently addressable microbiosensor array: What are the limits of sensing element density ?" Faraday Discuss., 2000, 116, 305-317.

Csoregi et al., "Design and Optimization of a Selective Subcutaneously Implantable Glucose Electrode Based on Wired' Glucose Oxidase," Anal. Chem., Apr. 1, 1995, vol. 67, No. 7, 1240-1244.

Wu et al., "Conjugation of Glucose Oxidase onto Mn-Doped ZnS Quantum Dots for Phosphorescent Sensing of Glucose in Biological Fluids," Anal. Chem., Feb. 15, 2010, vol. 82, No. 4, 1427-1433.

International Search Report and Written Opinion mailed Dec. 26, 2012 in corresponding PCT/US2011/062951 filed Dec. 1, 2011.

Rahman et al., "Functionalized Conducting Polymer as an Enzyme-Immobilizing Substrate: An Amperometric Glutamate Microbiosensor for in Vivo Measurements," Anal. Chem., Aug. 1, 2005, vol. 77, No. 15, 4854-4860.

International Preliminary Report on Patentability mailed Jun. 13, 2013 in corresponding PCT/US2011/062951 filed Dec. 1, 2011.

* cited by examiner

| Name; depth | Before | After |
|---|---|---|
| CQ-F 2 mm | | |
| CQ-G 4 mm | | |
| CQ-C 6mm | | |
| CQ-D 8mm | | |

Figure 5a

| Name; depth | Before | After |
|---|---|---|
| QA 2mm |  |  |
| QJ 4mm |  |  |
| QK 6mm |  |  |
| QH 8mm |  |  |

| Name; depth | Before | After |
|---|---|---|
| BS-C 4mm | | |
| BS-A 8mm | | |

FIG. 5C

TISSUE IMPLANTABLE MICROBIOSENSOR

RELATED APPLICATIONS

This application is a national stage application, under 35 U.S.C. §371, of International Patent Application No. PCT/US2011/062951, filed Dec. 1, 2011, and published as WO 2012/075331 on Jun. 7, 2012, which claims the priority benefit of U.S. Provisional Application No. 61/418,642, filed Dec. 1, 2010, both of which are hereby incorporated by reference in their entirety.

FIELD OF INVENTION

The present invention is directed to implantable biosensors and methods of production thereof. The biosensors are preferably fabricated using enzymes, and especially oxidase enzymes such as glucose oxidase. The enzymes are preferably immobilized on a nanoparticle. The biosensors may be fabricated with a single sensing element or fabricated as part of an array containing multiple, individually addressable sensing elements.

BRIEF DESCRIPTION OF THE DRAWING FIGURES

FIG. 1a. A schematic illustrating a biosensor prepared in accordance with the present invention. As described below, the coating and insulating layer are optional components of the biosensor system.

Figure 1B:
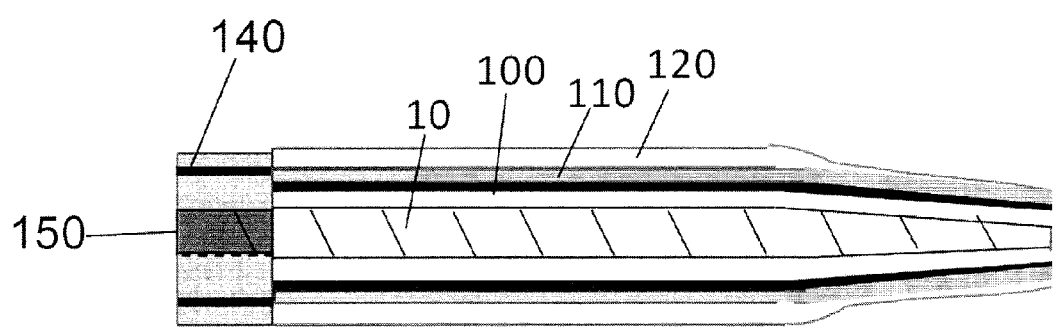

FIG. 1b. A schematic illustrating the biosensor housed in an alternative tapered cannula without the integrated reference electrode.

Figure 1C:
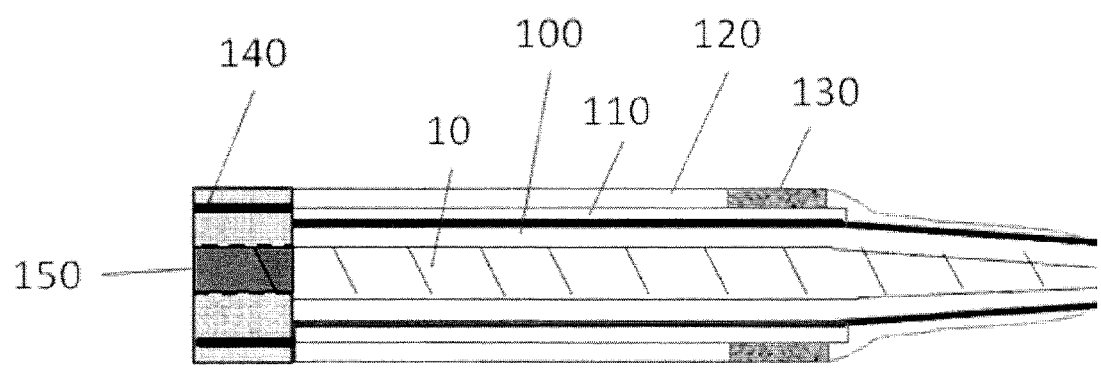

FIG. 1c. A schematic illustrating the biosensor housed in a tapered cannula with the integrated reference electrode. As described below, the cannula and conducting layer for the reference electrode coating are optional components of the biosensor system.

Figure 1D:
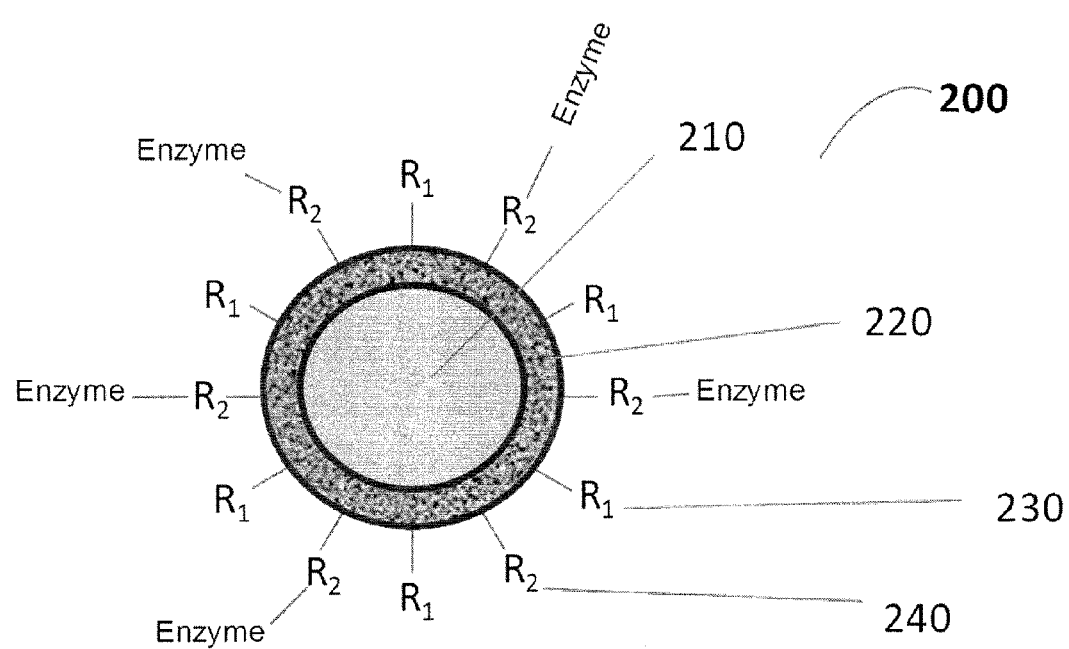

FIG. 1d. A schematic illustrating an exemplary enzyme immobilized core-shell nanoparticle.

Figure 1E:
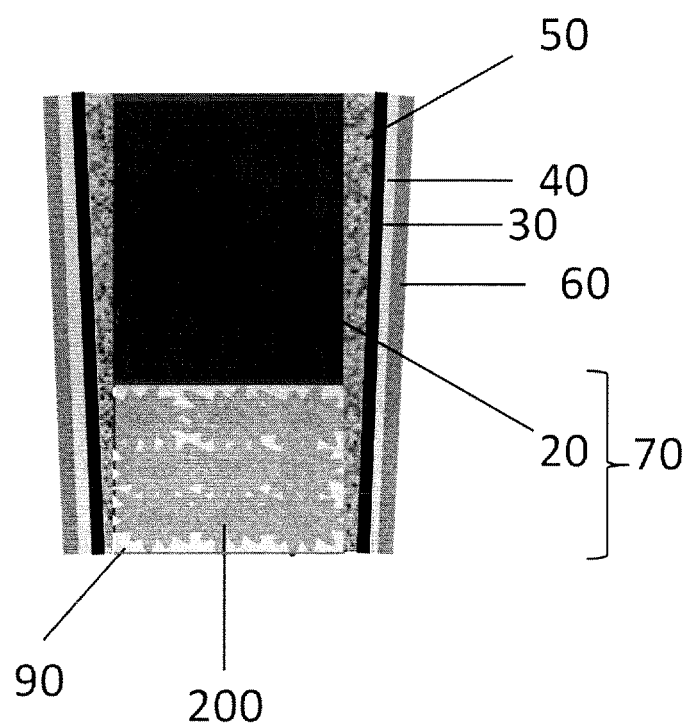

FIG. 1e. A schematic diagram of the capillary-based microcavity biosensor with magnetic nanoparticles engineered enzyme design.

Figure 2:
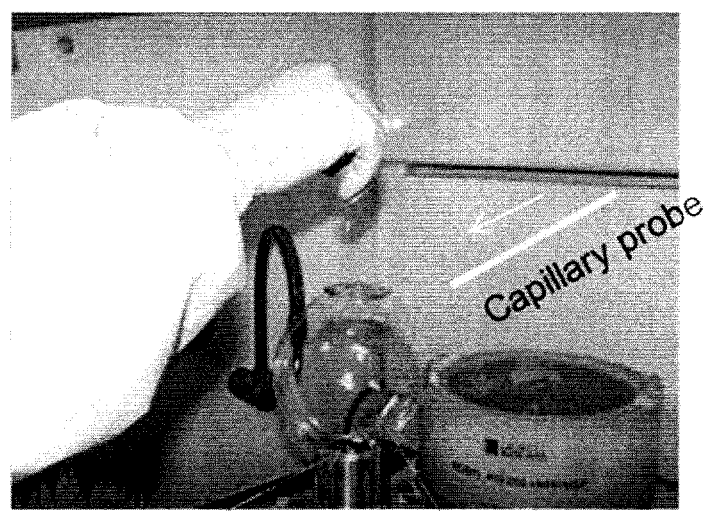

FIG. 2. An illustration of the apparatus used to coat the capillary substrate.

Figure 3:
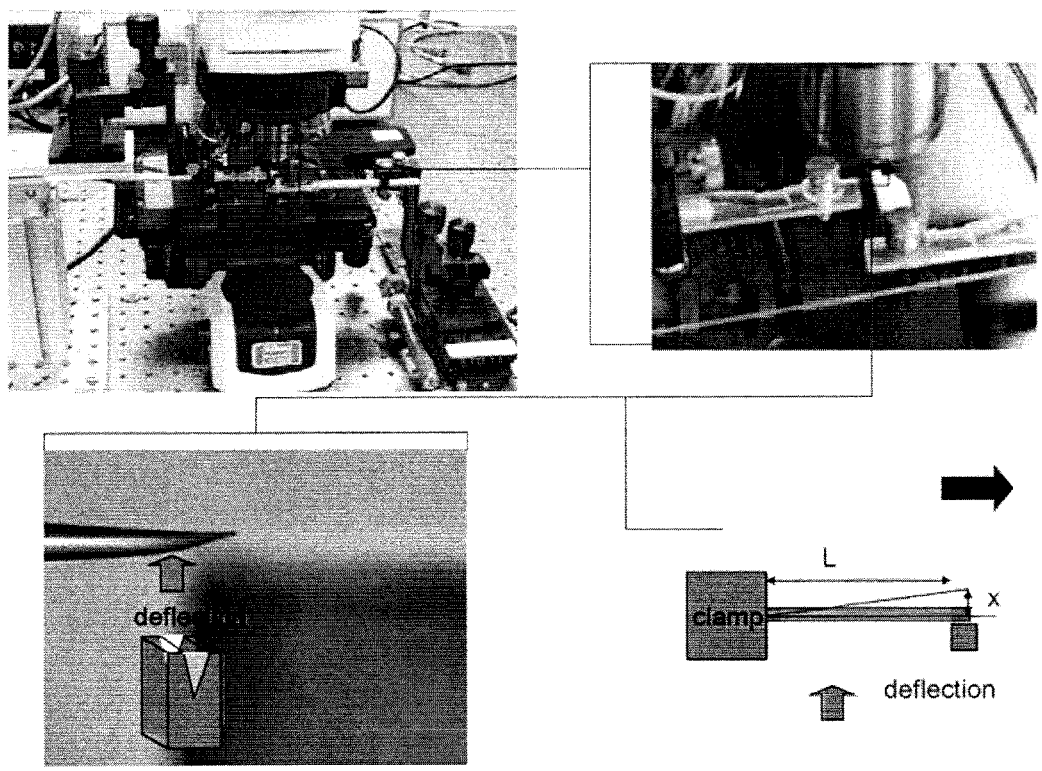

FIG. 3. An illustration of the set-up for the probe stress measurement.

Figure 4:
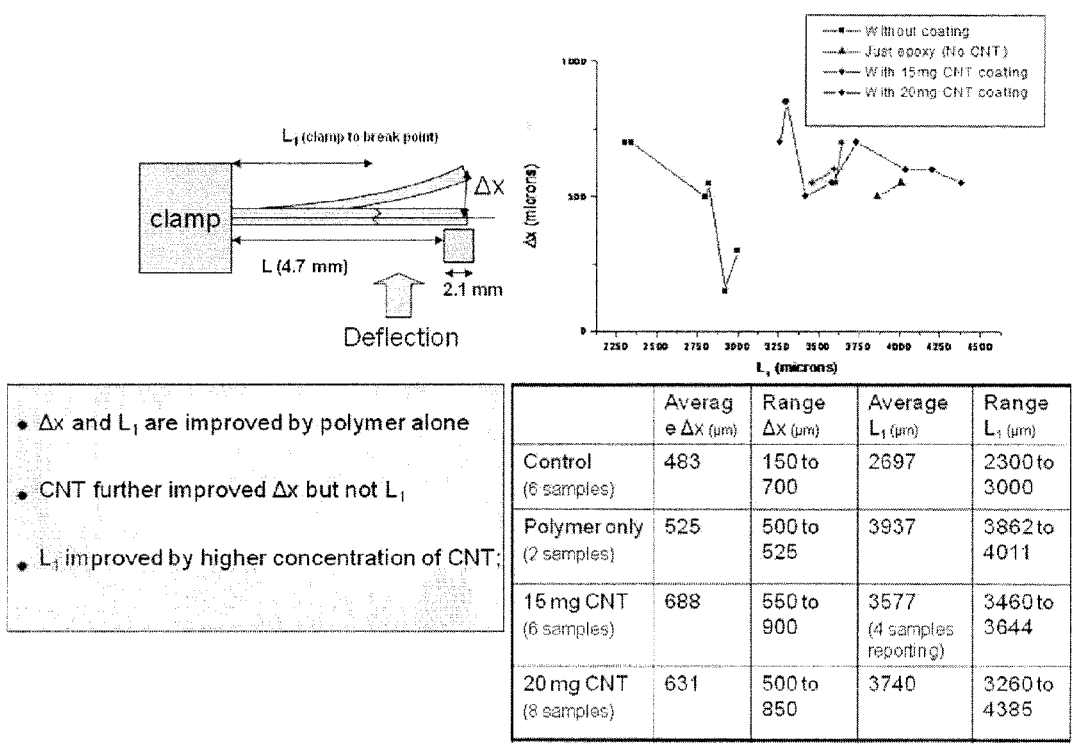

FIG. 4. An illustration of the results of stress tests performed on polymer and carbon nanotube ("CNT") coated substrate capillaries.

FIG. 5a. An illustration of the implantation experiment results of coated quartz microcapillary substrates. CQ refers to coated quartz, and the designations of F, G, C, and D refer to probes fabricated under the same conditions.

Figure 5B:
Figure 5B:
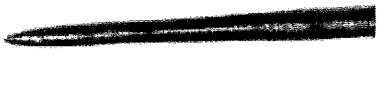
Figure 5B:
Figure 5B:
Figure 5B:
Figure 5B:
Figure 5B:
Figure 5B:

FIG. 5b. An illustration of the implantation experiment results of uncoated quartz microcapillary substrates. Q refers to the uncoated quartz probes, and the designations of A, J, K, and H refer probes fabricated under the same conditions.

Figure 5C:
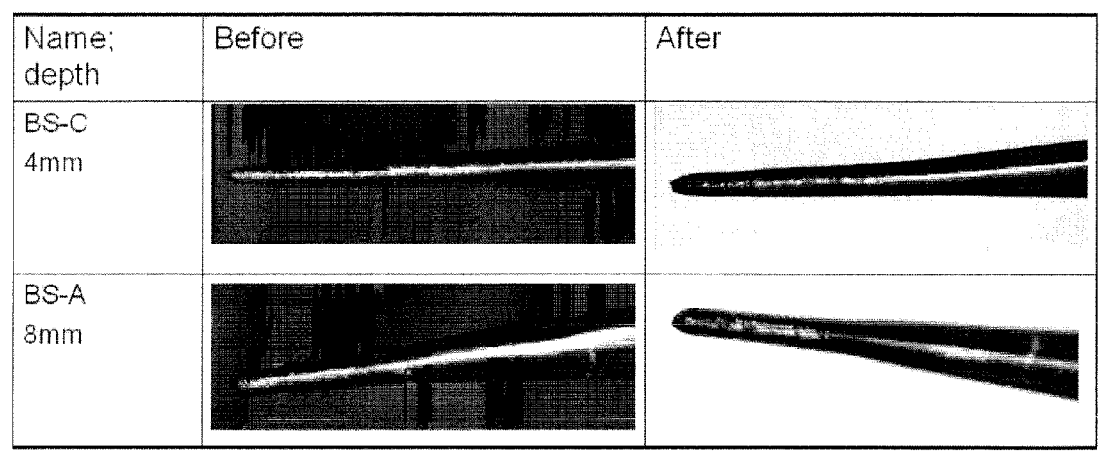

FIG. 5c. An illustration of the implantation experiment results of uncoated borosilicate glass microcapillary substrates. BS refers to uncoated borosilicate probes, and the designation of C and A refers to one of many probes fabricated under the same conditions.

FIG. 6a. An image taken of the substrate capillarity using a scanning electron microscope ("SEM") showing the cavity tip.

FIG. 6b. An image of the substrate capillary taken using an SEM showing the cavity tip.

FIG. 6c. SEM image of the capillary substrate with $Fe_3O_4$ nanoparticles with covalently attached glucose oxidase deposited for 120 seconds FIG. 6d. SEM image of the capillary substrate with $Fe_3O_4$ nanoparticles with covalently attached glucose oxidase deposited for 240 seconds FIG. 6e. SEM image of $Fe_3O_4$ nanoparticles with covalently attached glucose oxidase.

Figure 7:
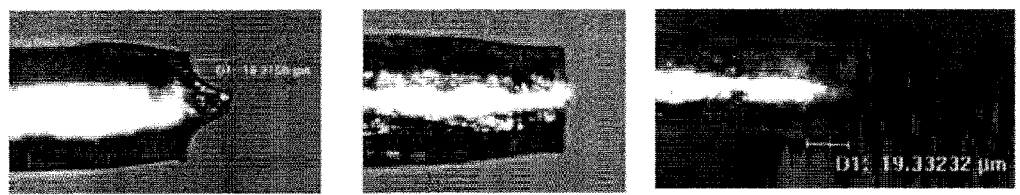

FIG. 7. SEM image of the tip position showing the distance from the edge of the glass to the tip of the platinum. In the exemplary SEMs, the tips protruded by 16 microns, flush, and recessed by 19 microns.

Figure 8:
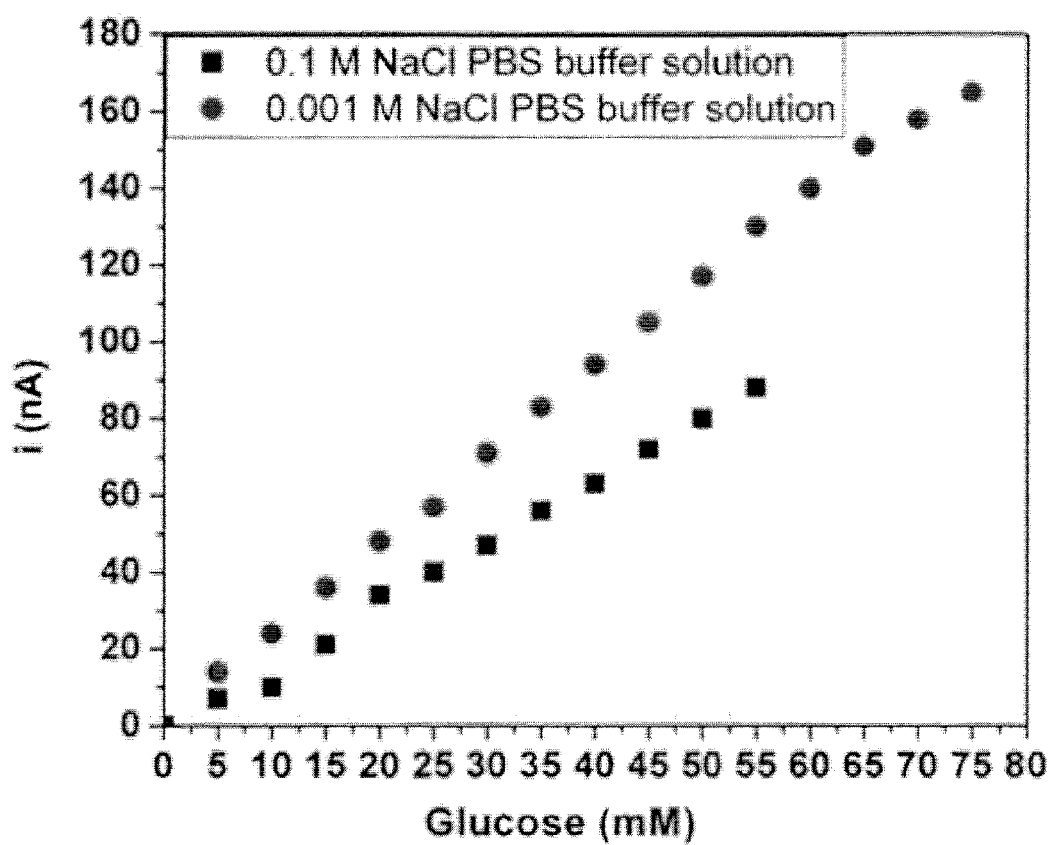

FIG. 8. Response graph showing the sensitivities of a biosensor response to glucose for different concentrations of NaCl (different ionic strengths) in the PBS buffer solution for deposition of $Fe_3O_4$ nanoparticles with covalently attached glucose oxidase.

Figure 9:
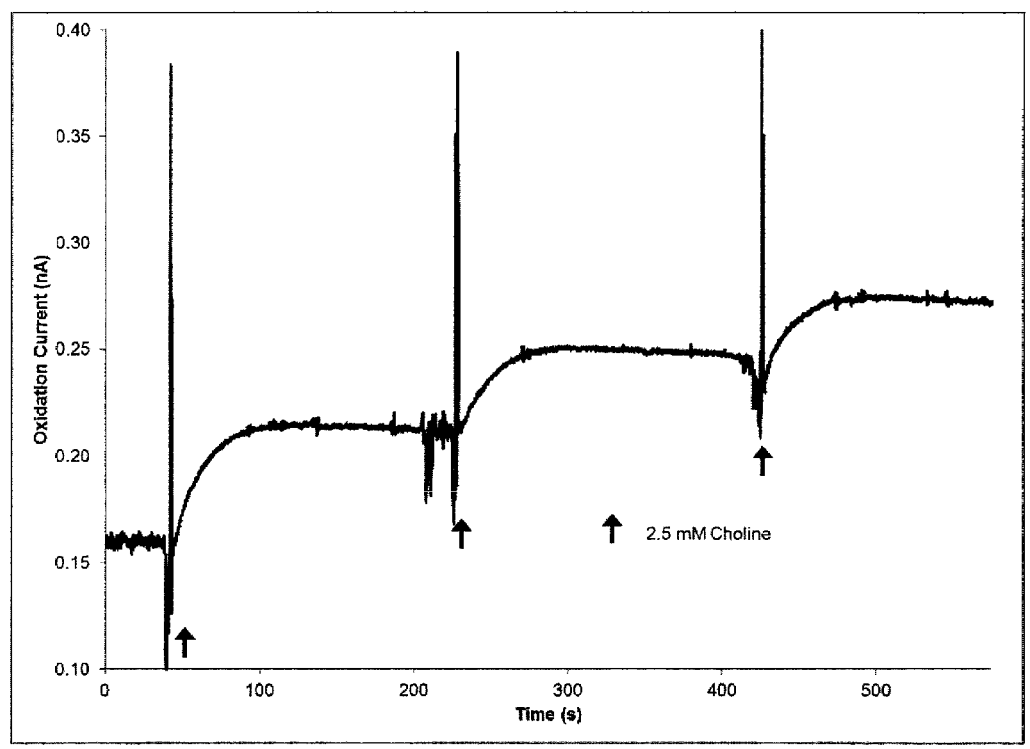

FIG. 9. A dose-response graph showing the response of the system to exogenously added choline. The magnetic iron-oxide nanoparticles were functionalized with covalently attached choline oxidase and were subsequently electrophoretically deposited into a capillary substrate.

Figure 10:
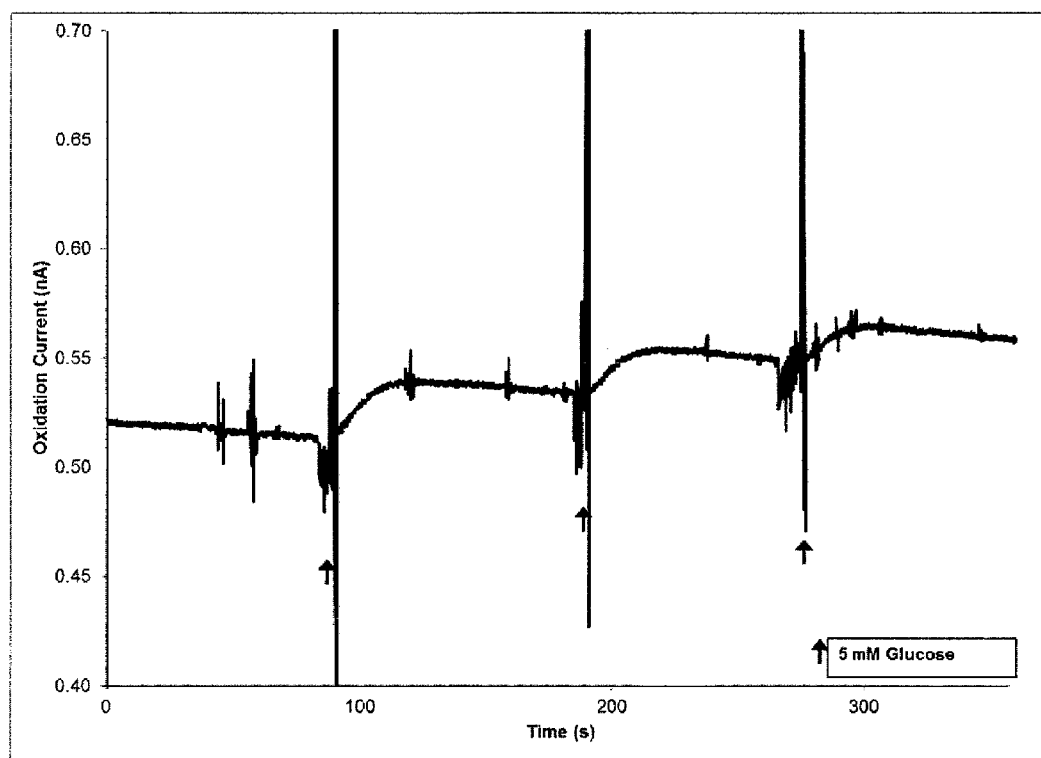

FIG. 10. A dose-response graph showing the response of the system to exogenously added glucose. The non-magnetic gold nanoparticles were functionalized with covalently attached glucose oxidase and were subsequently electrophoretically deposited into a capillary substrate.

Figure 11:
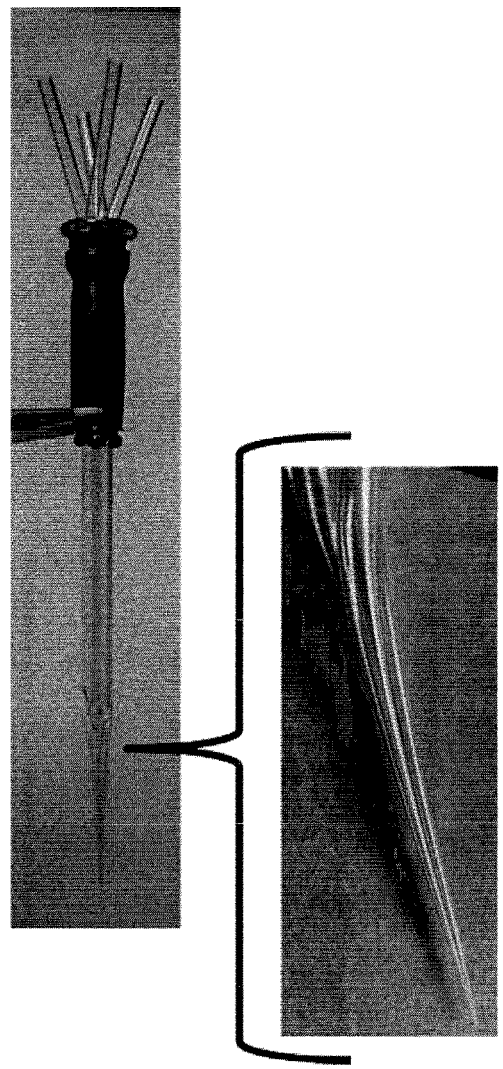

FIG. 11. A four-capillary substrate fashioned into a single unit with up to four independently addressable cavities or three independently addressable cavities and one drug delivery microinjection port suitable for drug delivery.

Figure 12:
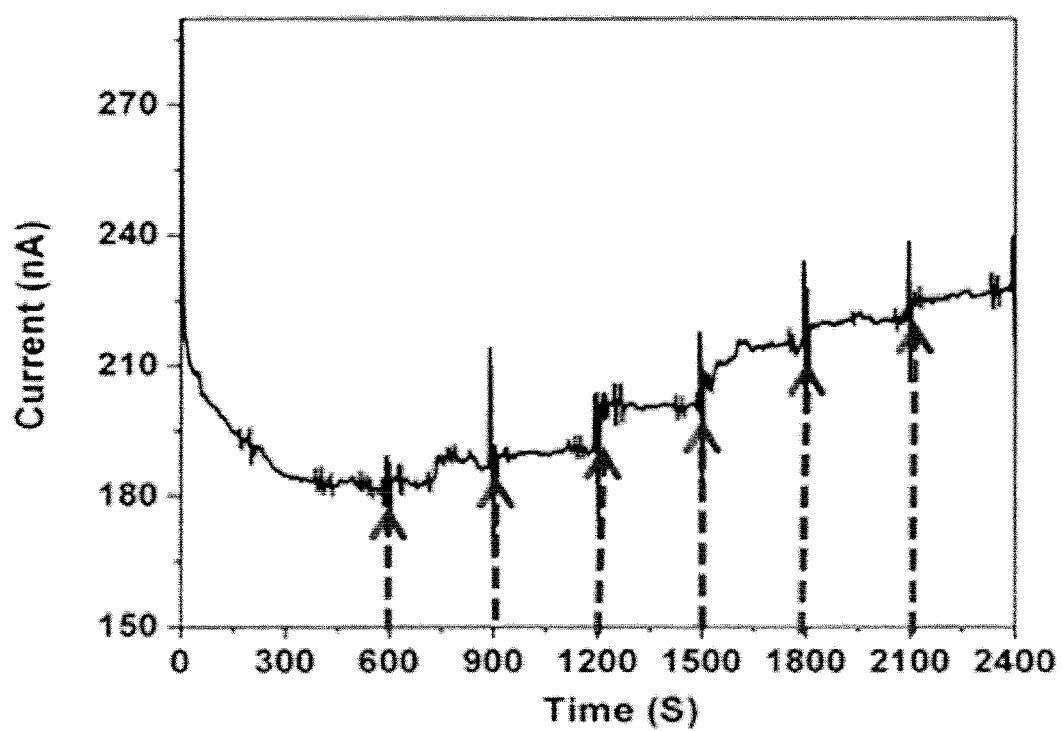

FIG. 12. A dose-response graph showing the response of the system to exogenously added glucose. The magnetic iron-oxide nanoparticles were functionalized with covalently attached glucose oxidase and were subsequently electrophoretically deposited into a capillary substrate. Current response of sensor made from the 0.1 M NaCl in the PBS buffer solution for deposition of $Fe_3O_4$ nanoparticles (50 nm) labeled with enzyme to the glucose of 5 mM added every 5 minutes at the time indicated by the arrows.

Figure 13:
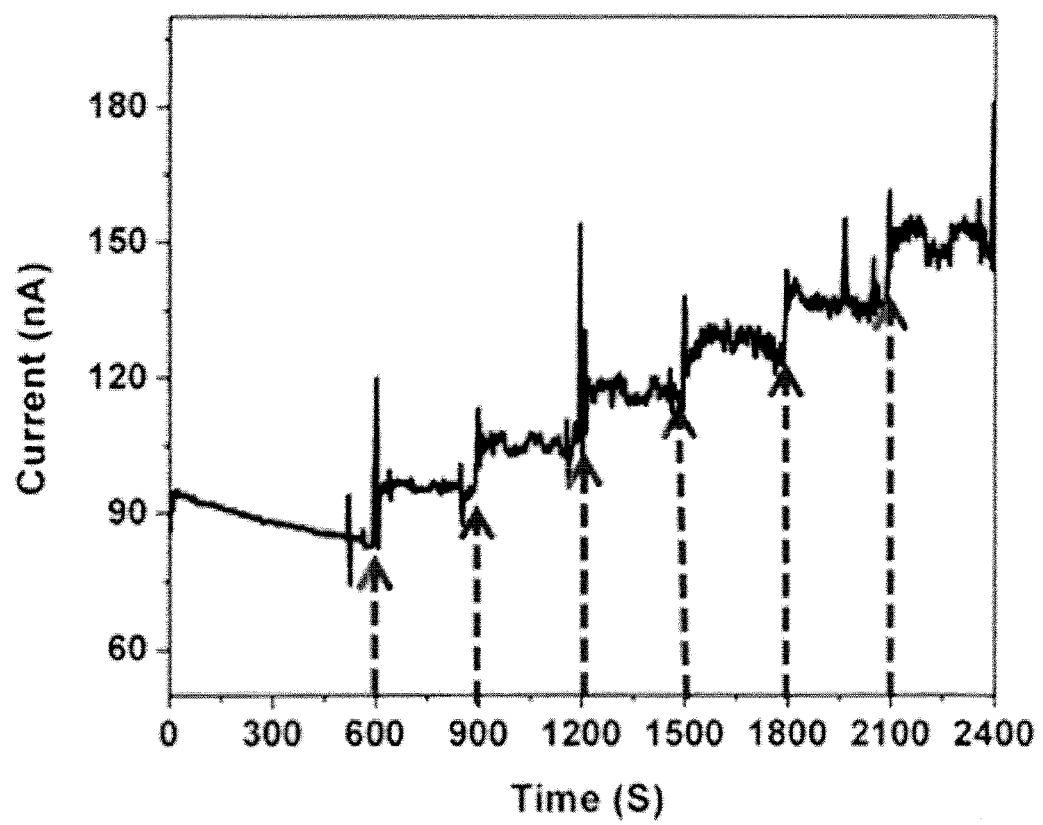

FIG. 13. A dose-response graph showing the response of the system to exogenously added glucose. The magnetic iron-oxide nanoparticles were functionalized with covalently attached glucose oxidase and were subsequently electrophoretically deposited into a capillary substrate. Current response of sensor made from the 0.001 M NaCl in the PBS buffer solution for deposition of $Fe_3O_4$ nanoparticles (50 nm) labeled with enzyme to the glucose of 5 mM added every 5 minutes at the time indicated by the arrows.

Figure 14:
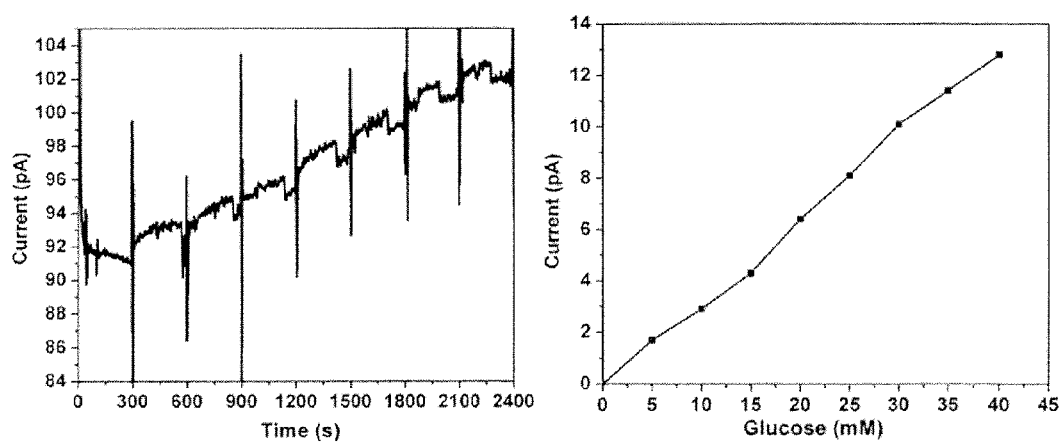

FIG. 14. A dose-response graph showing the response of the system to exogenously added glucose. The magnetic iron-oxide nanoparticles were coated with dextran and subsequently were functionalized with covalently attached glucose oxidase. The nanoparticles were then electrophoretically deposited into a capillary substrate.

Figure 15:
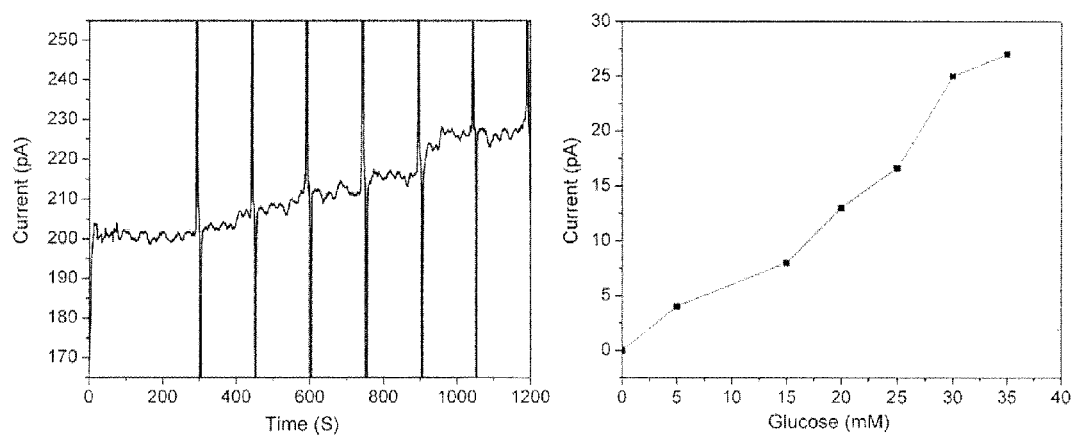

FIG. 15. A dose-response graph showing the response of the system to exogenously added glucose. The magnetic iron-oxide nanoparticles were coated with carbon graphite and subsequently were functionalized with covalently attached glucose oxidase. The nanoparticles were then electrophoretically deposited into a capillary substrate.

SUMMARY OF THE INVENTION

The present invention is directed to a tissue implantable biosensor system. The system includes a capillary substrate.

A conductive electrode is positioned within the capillary substrate to form a cavity at one end. The conductive electrode preferably comprises a metal or metal alloy wire which is sealed in the capillary substrate and etched to a depth to form the cavity. A plurality of nanoparticles having an enzyme immobilized thereon are deposited the cavity. The system also includes a reference electrode which may be located external to the biosensor system or integrated therein. Multiple capillary substrates may be fabricated into an array such that each cavity therein may contain a different enzyme and each cavity therein may be individually and independently addressable.

In one aspect of this invention, the capillary substrate has an exterior surface coated with a reinforcing material coating, which is typically about 2 to 100 nm thick. The reinforcing material is preferably selected from the group consisting of a para-aramid polymer coating, carbon nanotube coating, or graphene coating. In one aspect, the reinforcing material forms an electric shield which reduces electrical noise in the system. If the reinforcing material is conductive, an insulating material overlies the reinforcing material.

In another aspect, the capillary substrate is housed in a cannula. In yet another aspect, the cannula is tapered.

In still another aspect, one or more layers are provided over the cannula. For example, a conducting layer may be placed over the cannula, which forms an electric shield around the biosensor to reduce electrical noise in the system. An insulating layer may also overlay the conducting layer. Further, a reference electrode may be integrated into the cannula. In another aspect of the invention, the cannula may be adapted for use with biosensors of any design which range in size from about 1 µm to 5 mm in diameter.

In one aspect, the nanoparticles having the enzyme immobilized thereon comprise a nanoparticle core and a coating having an activated group for covalent attachment of the enzyme to the nanoparticle core. In another aspect, the nanoparticle core comprises a metal or metal alloy. In another aspect, the nanoparticle core is magnetic. In yet another aspect, the nanoparticle core is non-magnetic. In still another aspect, the nanoparticles are about 30 nm to 200 nm in diameter. In a further aspect, the coating comprises non-conductive material. In yet another aspect of the invention, the coating comprises a carbohydrate polymer, which is preferably linear. In still another aspect, the coating comprises a polymer selected from the group consisting of glycosaminoglycans (including hyaluronan, chondroitin, chondroitin sulfate, heparin, heparan sulfate, dermatan, dermatan sulfate, keratan, keratan sulfate), mucopolysaccharides, celluloses, pectins, glucomannans, galactomannans, agars, alginic acids, chitins, inulins, glucans, and amyloses, amylopectins, xanthan gums, dextrans, glycogens, and arabinoxylans. In yet another aspect, the coating is from about 5 to about 10 nm thick. In still a further aspect, the enzyme is attached to the nanoparticle or the nanoparticle coating via a primary amine, carboxylate, thiol, or aldehyde mioety. The charge on the nanoparticles is preferably tailored so that the zeta potential allows for electrodeposition of the nanoparticles into the small cavity of the biosensor, which is typically in the picoliter and sub-picoliter range.

In a further aspect, a tissue implantable cannula system is provided, which is suitable for use with biosensors beyond those specifically described herein. The system comprises a cannula comprising a shaft configured to accommodate at least one biosensor, an optional stylet to occupy the space within the shaft when the biosensor is absent (i.e., before the biosensor is introduced into the shaft during use of the system), a reference electrode integrated into the cannula, an electrical circuit external to the cannula, and a mechanism (e.g., coaxial or simple twisted pair electrical connections) to connect the reference electrode to the external electrical circuit.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF PREFERRED EMBODIMENT

The following abbreviations are defined for the purposes of this application: nm=nanometer; µm=micrometer; mm=millimeter; cm=centimeter; pL=picoliters; µL=microliters; mL=milliliters; mV=millivolts; µM=micromolar; mM=millimolar; BSA=bovine serum albumin.

By definition a resin is a sealing material and includes epoxies, glues, UV-activated glues and other materials that can form a seal.

The present invention is directed to an enzyme-based biosensor for measuring the concentration, concentration change or flux of an analyte. The term "analyte" refers to a substance or chemical constituent in a biological fluid (e.g., blood or urine) that can be analyzed. In general, the analyte may include any substance having an enzyme-based biorecognition element which produces an electrochemically active byproduct by the enzyme. Preferred analytes for detection by enzyme-based biosensors of the invention include any analyte that may be electrochemically inactive, i.e., does not readily undergo reaction at an electrode to produce a detectable current, but is acted upon by an enzyme to generate a species that is detectable by an electrode. Alternatively, the enzyme catalyzes a selective oxidation where otherwise electroactive analytes could not be distinguished. Examples of such analytes include, but are not limited to, biologically significant molecules such as glucose, lactate, and glutamate.

The present invention is broadly concerned with the crafting and manufacturability of an implantable enzymatic-based sensor characterized by a small size, optimum geometry, linearity of response over the concentration range of interest, extended shelf-life, selectivity for the analyte in question, and the ability to exclude bioactive interferents. More particularly, it is preferably concerned with a general approach to produce biosensors of the type designed to provide, and in conjunction with a suitable signal processing unit, a current which is proportional to the concentration of the analyte of interest. The biosensors described herein may be implanted in vivo, including intra-cerebral, sub-cutaneous, intra-muscular, inter-peritoneal, oral, serum, and vascular implantation, the majority of which may act as a surrogate for systemic monitoring and used to monitor analytes of interest in real-time. Multiple biosensors can be joined together to allow for the simultaneous recording of multiple analytes of interest. In addition to the in vivo applications, sensors of the design described herein may also find use in medical monitoring, industrial processes, fermentation, environmental monitoring, and waste water stream monitoring.

The biosensor 10 of the present invention is generally depicted in FIG. 1a. The biosensor includes a conductor 20 secured in a capillary substrate 30. The capillary substrate is preferably coated with one or more reinforcing materials 40. Typically, the capillary substrate is drawn from a piece of borosilicate glass or quartz using a commercially available laser-controlled or tungsten-filament capillary puller. This is a standard procedure in electrophysiological measurements. The capillary substrate may be tapered and is often drawn to a tip. The outside diameter ("OD") of the capillary substrate may be up to several hundred microns, but is preferably less than about 50 µm, and still more preferably less than 40 µm. In one aspect, the OD of the capillary substrate is about 20 to 40 µm at the tip, with an OD of 20 µm to 30 µm being most preferred. Thus, for example, the OD of the capillary substrate at the tip may be about 20 µm, 25 µm, or 30 µm. The tapered length of the capillary substrate 30 is typically about 2 mm to about 4 mm from the tip. The diameter of the capillary at the non-sensing end can range from 0.2 mm to about 1 mm in diameter.

As shown in FIG. 1, the biosensor 10 includes an electrical conductor 20, which is typically a conductive material sealed in the capillary substrate cavity. Preferably, the conductor 20 is a metal or metal alloy (Pt or Pt—Ir, for example). The conductor is typically a metal wire which is sealed in the cavity and then etched to a defined depth. The depth of the cavity 70 can be controlled precisely using etching procedures, and is typically in the range from about 1 µm to about 5 µm. Alternatively, a carbon fiber is sealed into the capillary substrate and diagonally cut off to form a disk which is then flush with the end of the capillary substrate as generally set forth in Feng, et al., *Electrochemical pretreatment of carbon fibers for in vivo electrochemistry: effects on sensitivity and response time*, Anal. Chem. 59, 1863-1867 (1987), which is incorporated by reference.

The gap between the capillary substrate 30 and the electrical conductor 20 is sealed with a sealing material 50 in order to define the true sensor area, which is defined as the cross sectional area of the wire exposed at the bottom of the cavity at the probe tip and generally surrounded by the sealing material. Suitable sealing materials include epoxies, UV-activated glues and other resins. In an exemplary embodiment, the HT resin mentioned above (FHI 3:1 HT Resin, from Fiberglass Hawaii) or a UV-activated epoxy (Type:Elc-4481, Part#82468, Batch#110824, from Electro-Lite Corp) was used for this purpose. A 31 gauge insulin syringe was used to inject the epoxy into the proximal end of the capillary substrate. The capillary substrate was then cured at room temperature for 24 hours or set by exposure to UV radiation for 15 seconds. The substrate was then cleaned by immersion in an ultrasonic bath for three minutes in a water, acetone, and methanol mixture.

Figure 6:
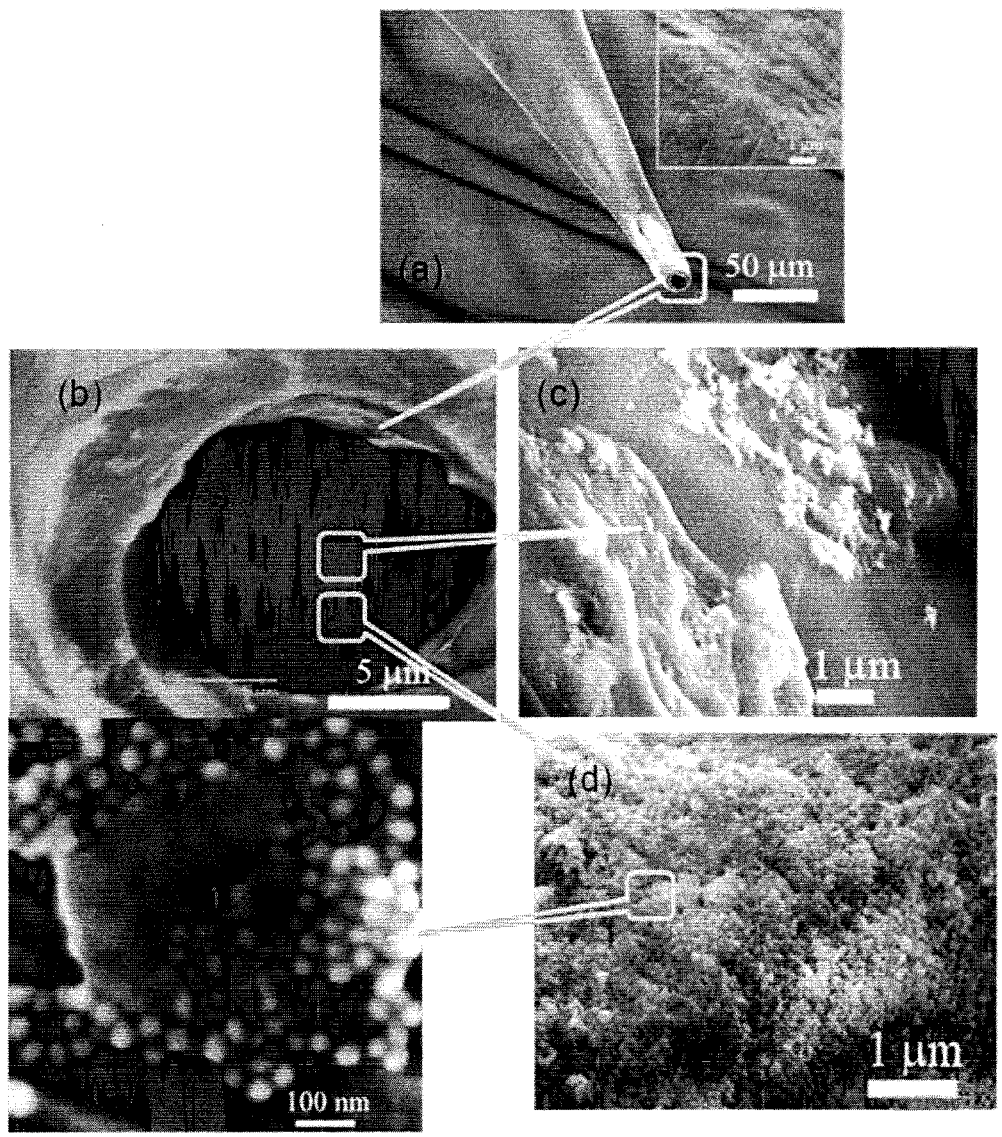

Etching of the conductor is generally known to those skilled in the art. Suitable etching methods are described in Jung, et al., *Oxygen microsensor and its application to single cells*, Anal. Chem. 71 3642-3649 (1999); Jung, et al, *Development and Application of a self-referencing glucose Microsensor*, Anal. Chem. 73 3759-3767 (2001); and Jung, et al., U.S. Pat. No. 6,802,957, all of which are incorporated by reference. FIG. 6 shows a capillary substrate with a Pt wire sealed therein and a cavity created by etching the Pt wire to a defined depth. The depth of the cavity can be controlled by the varying the etching parameters including etching time, which may be varied from a few milliseconds to several minutes depending upon the desired depth.

In order to strengthen the very small capillary substrate 30, the capillary substrate is preferably coated with a reinforcing material coating 40 of high tensile strength. Exemplary materials include various polymers and composite coatings (for example, FHI 3:1 HT Resin, from Fiberglass Hawaii), as well various nanocomposites, for example, nanoparticle, graphene, carbon nanotube ("CNT")-polymer composite coatings. Coating of the polymer and nanocomposites can be made following the procedure described in prior art by G. Yu, A. Cao and C. M. Lieber, Nature Nanotechnology 2, 372 (2007), which is incorporated by reference. As shown in FIG. 2, on the apparatus, a thin layer of polymer or nanocomposite is generated over a large ring and the thickness of the layer is controlled through several processing parameters. Pressure is applied to generate the thin layer on the ring, which is typically in the range of 15 to 25 psi, although higher pressures may be needed for certain epoxies. The coating on the capillary probe is made by penetrating the probe through the polymer layer suspended on the ring. Multiple coatings may be used to reach larger total thickness of the coating on the capillary.

The thickness of coating 40 may vary depending on the type of the reinforcing material and the diameter of the capillary substrate. Typically, the coating thickness ranges between from about 2 nm to about 100 nm, for example 10 nm, 20 nm, 30 nm, 40 nm, 50 nm, 60 nm, 70 nm, 80 nm, 90 nm, or 100 nm or some range in between. The coating total thickness may be controlled by the number of layers coated.

As shown in FIG. 1, the biosensor 10 may optionally include an insulating layer 60, which is typically used if the reinforcing layer 40 is conducting. Further, the biosensor 10 may include an electrical connection to the reinforcing layer 40 if it is comprised of a conducting material.

FIG. 3 shows the schematic of an apparatus that was used for testing the mechanical properties of capillary probes. A deflection force is applied to the tip of a clamped probe by a square rod (dimension: 2.1 mm) with a groove at the tip to avoid slippage of the probe during deflection. The procedure is recorded with increasing deflection $\Delta x$ until the probe breaks using a CCD camera attached to an optical microscope. The $\Delta x$ and L values at the breaking point for 22 probes tested are included in the table and chart. As shown in FIG. 4, the general trend observed was that the coated probes withstood larger lateral deflections. For example, a 25 to 40 µm diameter capillary substrate so coated can withstand significantly larger lateral deflections by up to 400% better and longitudinal breaking length measured from the tip by up to 80% compared to the uncoated capillary substrate.

In order for the biosensors of this invention to function in vivo, said biosensors must survive implantation in tissue. To test survivability of the capillary substrates upon implantation, said capillary substrates fashioned from quartz CNT coating, quartz probes with a 20 mg CNT coating, and borosilicate probes were prepared for this experiment using the above protocols. All capillary substrates had taper lengths between from about 2 mm to about 4 mm. Each probe was mounted a stereotaxic manipulator and pressed into mouse brain cadaver tissue to depths ranging from about 2 mm to about 8 mm. After removal from the tissue, the probes were assessed for damage (FIGS. 5a-5c). This demonstrated that this design can be inserted in the mouse brain without damaging the capillary substrate (100% survival rate of probes tested).

CNT and graphene are conductors and each might serve as a coaxial shield for the sensor, thus reducing noise and dielectric absorption effects on the sensor signal. Other coatings include aromatic polyamides, such as para-aramids, which are well known for their strength, and could alternatively be used as a coating as they have been demonstrated to be biocompatible in certain devices.

Although not required, as generally shown in FIG. 1b and FIG. 1c, the biosensor 10 may be housed in a non-conductive cannula 100. The cannula is preferably tapered, and examples of such tapered cannulas are generally disclosed in Martin et al., U.S. Pat. No. 7,076,987, which is incorporated by reference. The cannula may be stereotaxically implanted as if it were the sensor and sealed in place with cement. A wire would be inserted so that it is flush with the end of the cannula and would remain in place until the sensor is inserted. According to standard practice, sensor implantation would occur after the tissue has had time to stabilize. The cannula would be placed at a depth that would permit the sensor to extend perhaps from about 10 to about 15 µm beyond the end of the cannula. Since the cannula is tapered, it would lend support to the sensor as it is inserted and while measurements are being made.

FIG. 1b illustrates first exemplary cannula made in accordance with the present invention. The non-conducting cannula 100 is preferably surrounded by an optional conducting layer 110 for the reference electrode (not shown; and located externally). The optional conducting layer 110 is preferably surrounded by an optional insulating layer 120. In addition, a contact 140 to the conducting layer 110 is provided. Electrical connection 150 is typically a plug which connects the sensor 10 to the external electronics (not shown).

In another exemplary embodiment, as generally shown in FIG. 1c, non-conducting cannula 100 is surrounded by a conducting layer 110 for the reference electrode 130. The conducting layer 110 is surrounded by an insulating layer 120. The reference electrode 130 is integrated into the cannula by forming the electrode on the outside of the cannula 100. The combination of these two will mimic a so-called Reference Electrode/Faraday Cage. FIG. 1c illustrates AgCl/Ag deposited on the outside of the cannula which serves as a reference electrode 130, as well as the conductive layer 110 for the reference electrode and insulating layer 120. In addition, a contact 140 for the reference electrode 130 is provided. Electrical connection 150 is typically a plug which connects the sensor 10 and reference electrode 130 to the external electronics (not shown).

The cannula 100 is preferably quite thin, and is typically on the order of a few hundreds of microns in OD, which is reduced to smaller dimensions at the tip. The length of the cannula may be in the range of several microns to millimeters, depending on the specific applications. The smoothness or roughness of the cannula may also vary. For example, many cannulas and needles used with other devices are smooth on the outside but inside have a very rough surface which can damage the sensor when it is inserted. The cannula fabrication procedure described herein can minimize the occurrence of a rough internal surface.

In one aspect, the cannula may be cast as a composite polymer-nanoparticle casting. In another aspect, a tapered metal (such as Cu) wire may be used to construct the tapered cannula 100 and other layers, such as those illustrated in FIG. 1b and FIG. 1c. Tapered metal (Cu) wires using electrochemical etching of the wire may be fabricated, during which time the wire impedance is monitored. The tapering length and tip diameter of the cannula can be controlled by selecting the etchant (liquid) geometry and terminating the process at a selected impedance value based on the impedance calibration curve. The tapering length is typically in the range of hundreds of microns to several millimeters and the tip diameter is typically in the range a few to several tens of microns, respectively using the procedures described in Wang & Wu, *Improved near-field scanning microwave microscopy in combination with transport measurement for characterization of nonuniformity of electrical dissipation in $YBa_2Cu_3O_{7-x}$ films of variable thickness*, J. Appl. Phys. 107 043905 (2010), which is incorporated by reference. In essence, such tapered metal wires will be used as a "mold" for polymer or CNT (graphene)-polymer composites of selected thickness used to construct cannula 100 and the various layers or coating around the cannula 100. The Cu mold can be partially or completely removed using controllable $FeCl_3$ etching. The procedure can also be modified if a different metal, ceramic, or other biocompatible material inner layer is desired for the tapered cannula. Direct coating of the selected materials on the Cu wire mold can be made before the Cu wire is removed. The selected materials, such as a polymer or a nanocomposite may be coated on the Cu mold using the same method described earlier to control layer thickness and the number of layers. The nanocomposite layer may be conducting and the conductivity can be controlled by choosing the volume portion of the CNT, graphene, or other nanoparticles doped. In addition, a metallic conducting layer may also be coated using vacuum based coating methods or electrical plating. Furthermore, a single layer of graphene may be grown on the Cu mold and may serve as a mechanical enhancing layer since the C—C bonds in graphene are very strong (the diamond bond). Other layers can then be coated on top of the graphene. The multilayered structure of the tapered cannula may provide flexibility for incorporation of different functionality in the cannula design.

The active area of the biosensor is very small. The biosensor will constitute a highly resistive (approximately $10^{11}$ ohms) circuit when coupled with a reference electrode in vivo. This may give rise to leakage (current paths other than those from working to reference electrode), electric noise coupling (local field potential and external field coupling), magnetic noise coupling (EMF induced by external noise sources such as 60 Hz power lines, and local magnetic field coupling), and electronics noise (pink, white, 1/f, shot, etc.). To provide a device capable of sensing in vivo in an untethered and relatively uncontrolled environment, a conductive coating of nanoparticles 110 may be used to mimic a Faraday Cage in form of the cannula itself as indicated above. In an exemplary embodiment, as generally shown in FIG. 1c, conductive nanoparticles 110 will be deposited on the outer surface of the cannula. This will then be coated with an insulating layer 120. On a bottom ring, silver will be deposited directly on the conductive nanoparticle layer and then oxidized to Ag/AgCl to form the reference electrode 130. In this way, electrical noise coupling will be controlled by the action of the cannula which mimics a Faraday cage; magnetic noise coupling will be controlled by the close proximity and known geometry of the reference/working electrode loop; and the user will be provided with a very simple and robust connection strategy. In other words, the idea is that the conductive layer 110 decreases electrical noise while virtually eliminating effects caused by charge leakage into and out of the insulating layers. The conducting layer 110 is connected to a ground point and will generally shield the entire system from external fields (60 Hz, local field potentials, etc.) that would otherwise degrade the signal to noise ratio.

The cavity 70 of the biosensor 10 serves as an enzyme-receiving zone. That is, in this cavity, one or more enzymes are deposited. Virtually any enzyme can be deposited on the biosensor electrode, depending upon the nature of the analyte to be detected. The most useful enzymes are the oxidase enzymes, such as those selected from the group consisting of malate oxidase, EC 1.1.3.3, co-factor(s)=FAD; hexose oxidase, EC 1.1.3.5, co-factor(s)=Cu; aryl-alcohol oxidase, EC 1.1.3.7, co-factor(s)=FAD; L-gulonolactone oxidase, EC 1.1.3.8, co-factor(s)=FAD; pyranose oxidase, EC 1.1.3.10, co-factor(s)=FAD; L-sorbose oxidase, EC 1.1.3.11, co-factor(s)=FAD(?)(?); pyridoxine 4-oxidase, EC 1.1.3.12, co-factor(s)=FAD; (S)-2-hydroxy-acid oxidase, EC 1.1.3.15, co-factor(s)=FAD, FMN; ecdysone oxidase, EC 1.1.3.16, co-factor(s)=NADPH; secondary-alcohol oxidase, EC 1.1.3.18, co-factor(s)=FAD(?)(?); 4-hydroxymandelate oxidase, EC 1.1.3.19, co-factor(s)=co-factor(s)=FAD(?)(?), $Mn^{2+}$; long-chain-alcohol oxidase, EC 1.1.3.20, co-factor(s)=FAD; thiamine oxidase, EC 1.1.3.23, co-factor(s)=FAD; hydroxyphytanate oxidase, EC 1.1.3.27. co-factor(s)=FAD(?)(?); N-acylhexosamine oxidase, EC 1.1.3.29, co-factor(s)=FAD(?)(?); polyvinyl-alcohol oxidase, EC 1.1.3.30, co-factor(s)=FAD(?)(?); D-Arabinono-1, 4-lactone oxidase, EC 1.1.3.37, co-factor(s)=FAD; vanillyl-alcohol oxidase, EC 1.1.3.38, co-factor(s)=FAD; D-mannitol oxidase, EC 1.1.3.40, co-factor(s)=FAD(?)(?); alditol oxidase, EC 1.1.3.41, co-factor(s)=FAD; choline dehydrogenase, EC 1.1.99.1, co-factor(s)=Coenzyme Q; gluconate 2-dehydrogenase EC 1.1.99.3, co-factor(s)=FAD; glucooligosaccharide oxidase, EC 1.1.99.B3, co-factor(s)=FAD; alcohol dehydrogenase, EC 1.1.99.8, co-factor(s)=PQQ; cellobiose dehydrogenase, EC 1.1.99.18, co-factor(s)=FAD; aldehyde oxidase, EC 1.2.3.1, co-factor(s)=FAD; glyoxylate oxidase, EC 1.2.3.5, co-factor(s)=FAD(?)(?); indole-3-acetaldehyde oxidase, EC 1.2.3.7, co-factor(s)=FAD; aryl-aldehyde oxidase, EC 1.2.3.9, co-factor(s)=ATP, NADPH; retinal oxidase, EC 1.2.3.11, co-factor(s)=FAD; abscisic-aldehyde oxidase, EC 1.2.3.14, co-factor(s)==MoCo; aldehyde ferredoxin oxidoreductase, EC 1.2.7.5, co-factor(s)==Ferredoxin tungsten co-factor; indolepyruvate ferredoxin oxidoreductase, EC 1.2.7.8, co-factor(s)=TPP; aldehyde dehydrogenase, EC 1.2.99.7, co-factor(s)=FE-molybdenum; dihydroorotate oxidase, EC 1.3.3.1, co-factor(s)=FAD-FMN; acyl-CoA oxidase, EC 1.3.3.6, co-factor(s)=FAD; dihydrouracil oxidase, EC 1.3.3.7, co-factor(s)=FMN; tetrahydroberberine oxidase, EC 1.3.3.8, co-factor(s)=FAD; tryptophan alpha,beta-oxidase, EC 1.3.3.10, co-factor(s)=(?); L-galactonolactone oxidase, EC 1.3.3.12, co-factor(s)=FAD; acyl-CoA dehydrogenase, EC 1.3.99.3, co-factor(s)=FAD; Isoquinoline-1-oxidoreductase, EC 1.3.99.16, co-factor(s)=iron-sulfur centre or molybdopterin cytosine dinucleotide; quinaldate 4-oxidoreductase, EC 1.3.99.18, co-factor(s)=FAD or pterin molybdenum co-factor; D-aspartate oxidase, EC 1.4.3.1, co-factor(s)=FAD; L-amino-acid oxidase, EC 1.4.3.2, co-factor(s)=FAD; monoamine oxidase, EC 1.4.3.4, co-factor(s)=FAD; pyridoxal 5'-phosphate synthase, EC 1.4.3.5, co-factor(s)=FMN; D-glutamate oxidase, EC 1.4.3.7, co-factor(s)=FAD; ethanolamine oxidase, EC 1.4.3.8; putrescine oxidase, EC 1.4.3.10, co-factor(s)=FAD; cyclohexylamine oxidase, EC 1.4.3.12, co-factor(s)=FAD; protein-lysine 6-oxidase, EC 1.4.3.13, co-factor(s)=lysyl-tyrosyl quinone; D-glutamate(D-aspartate) oxidase, EC 1.4.3.15, co-factor(s)=FAD; L-lysine 6-oxidase, EC 1.4.3.20, co-factor(s)=(?); primary-amine oxidase, EC 1.4.3.21, co-factor(s)=2,4,5-trihydroxyphenylalanine quinone; 7-chloro-L-tryptophan oxidase, EC 1.4.3.23, co-factor(s)=FAD; N-methyl-L-amino-acid oxidase, EC 1.5.3.2, co-factor(s)=FAD; non-specific polyamine oxidase, EC 1.5.3.B2, co-factor(s)=FAD; N8-acetylspermidine oxidase (propane-1,3-diamine-forming), EC 1.5.3.B3, co-factor(s)=FAD; N6-methyl-lysine oxidase, EC 1.5.3.4, co-factor(s)=FAD; polyamine oxidase (propane-1,3-diamine-forming), EC 1.5.3.B4, co-factor(s)=FAD; N1-acetylpolyamine oxidase, EC 1.5.3.B5, co-factor(s)= FAD; spermine oxidase, EC 1.5.3.B6, co-factor(s)=FAD; pipecolate oxidase, EC 1.5.3.7, co-factor(s)=FAD; dimethylglycine oxidase, EC 1.5.3.10, co-factor(s)=FAD; polyamine oxidase, EC 1.5.3.11, co-factor(s)=FAD+Fe; Dihydrobenzophenanthridine oxidase, EC 1.5.3.12, co-factor(s)=FAD+Cu; NAD(P)H oxidase, EC 1.6.3.1, co-factor(s)=FAD+HEME+Ca; urate oxidase, EC 1.7.3.3; 3-acinitropropanoate oxidase, EC 1.7.3.5, co-factor(s)=FMN; sulfite oxidase, EC 1.8.3.1, co-factor(s)=HEME, OLYBDOPTERIN; methanethiol oxidase, EC 1.8.3.4; prenylcysteine oxidase, EC 1.8.3.5, co-factor(s)=FAD; L-ascorbate oxidase, EC 1.10.3.3, co-factor(s)=HEME+CU; 3-hydroxyanthranilate oxidase, EC 1.10.3.5, co-factor(s)=Fe; rifamycin-B oxidase, EC 1.10.3.6, co-factor(s)=(?); superoxide dismutase, EC 1.15.1.1, co-factor(s)=(?); reticuline oxidase, EC 1.21.3.3, co-factor(s)=FAD; lactate oxidase, L-EC 1.1.3.15, co-factor(s)=FAD, FMN; D-amino acid oxidase, EC 1.4.3.3, co-factor(s)=FAD; (S)-6-hydroxynicotine oxidase, EC 1.5.3.5, co-factor(s)=FAD; (R)-6-hydroxynicotine oxidase, EC 1.5.3.6, co-factor(s)=FAD; alcohol oxidase, EC 1.1.3.13, co-factor(s)=FAD; pyruvate oxidase, EC 1.2.3.3, co-factor(s)=FAD, TPP; glucose oxidase, EC 1.1.3.4), co-factor(s)=FAD; L-glutamate oxidase, EC 1.4.3.11, co-factor(s)=FAD; acyl coenzyme A oxidase, EC 1.3.3.6, co-factor(s)=FAD; choline Oxidase, EC 1.1.3.17, co-factor(s)=FAD; glutathione sulfhydryl oxidase, EC 1.8.3.3, co-factor(s)=FAD; glycerolphosphate oxidase, EC 1.1.3.21, co-factor(s)=FAD; sarcosine oxidase, EC 1.5.3.1, co-factor(s)=FAD; xanthine oxidase, EC 1.1.3.22, co-factor(s)=FAD; oxalate oxidase, EC 1.2.3.4, co-factor(s)= $Mn^{2+}$; cholesterol oxidase, EC 1.1.3.6, co-factor(s)=FAD; gamma-glutamyl-putrescine oxidase, EC undefined, obtained from *Escherichia coli* K12, co-factor(s)=FAD— capable of oxidizing GABA; GABA oxidase, EC undefined, obtained from: *Penicillium* sp. KAIT-M-117, co-factor(s)=FAD(?)(?); histamine oxidase (diamine oxidase), EC 1.4.3.22, co-factor(s)=pyrroloquinoline, quinone, FAD, others; nucleoside oxidase, EC 1.1.3.39, co-factor(s)=FAD; L-lysine oxidase, EC 1.4.3.14, co-factor(s)=FAD; L-aspartate oxidase, EC 1.4.3.16, co-factor(s)=FAD; glycine oxidase, EC 1.4.3.19, co-factor(s)=FAD; and galactose oxidase, EC 1.1.3.9, co-factor(s)=pyrroloquinoline, quinone. The (?) entry indicates that the co-factor is either completely unknown, or that the indicated co-factor has not been verified.

A list of preferred members of this group of enzymes includes:

Lactate oxidase, EC 1.1.3.15 or EC 1.13.12.4; D-amino acid oxidase, EC 1.4.3.3; (S)-6-hydroxynicotine oxidase, EC 1.5.3.5; Alcohol Oxidase, EC 1.1.3.13; Pyruvate oxidase, EC 1.2.3.3; Glucose oxidase, EC 1.1.3.4; Glutamate oxidase, EC 1.4.3.11; Acyl coenzyme A oxidase, EC 1.3.3.6; Glutathione sulfhydryl oxidase, EC 1.8.3.3; Choline oxidase, EC 1.1.3.17; Glyceroiphosphate oxidase, EC 1.1.3.21; Sarcosine oxidase, EC 1.5.3.1; Xanthine oxidase, EC 1.1.3.22; Oxalate oxidase, EC 1.2.3.4; Cholesterol oxidase, EC 1.1.3.6; Gamma-glutamyl-putrescine oxidase; Histamine oxidase (diamine oxidase); Nucleoside oxidase, EC 1.1.3.39; L-Lysine oxidase, EC 1.4.3.14; L-Aspartate oxidase, EC 1.4.3.16; Glycine oxidase, EC 1.4.3.19; and Galactose oxidase, EC 1.1.3.9.

The invention may also utilize new oxidoreductases that may find utility in measuring analytes for which no oxidoreductase presently exists. New oxidoreductases with new or altered analyte activities, specificities, and selectivities may be derived from natural sources, derived by the conversion of an existing oxidoreductase via standard molecular biology mutagenesis techniques or derived by the directed evolution of an existing enzyme. The new oxidoreductase would have activity, selectivity, and specificity for an analyte not presently available. Such analytes that would benefit from the discovery of a new oxidoreductase are selected from the list consisting of nicotine, caffeine, cocaine, amphetamine, cortisol, corticosterone, dopamine, serotonin, norepinephrine, L-DOPA, GABA, ATP, and acetylcholine. While some of these analytes may be the substrate of an existing oxidoreductase (e.g., (S)-6-hydroxynicotine oxidase has some activity for nicotine; gamma-glutamyl putrescence oxidase has some activity for GABA), said analytes are not the primary substrate for said oxidoreductase.

The cavity 70 is quite small, for example from about 1 μm to about 5 μm deep with a diameter of about 1 μm to about 100 μm, and more preferably, with a diameter from about 5 μm to about 20 μm e.g., about 5 μm, 6 μm, 7 μm, 8 μm, 9 μm, 10 μm, 11 μm, 12 μm, 13 μm, 14 μm, 15 μm, 16 μm, 17 μm, 18 μm, 19 μm, 20 μm. The volume of the cavity 70 typically ranges between from about 0.001 pL to about 5 pL (e.g., 0.001 pL, 0.01 pL, 0.1 pL, 1.0 pL).

Multiple capillary substrates may be fabricated into an array such that each cavity therein may contain a different enzyme and each cavity therein may be individually and independently addressable. The present invention uses electrophoretic deposition to deliver a very small amount of enzyme to an electrochemically addressable array element. Further, this technique permits the development of sensor arrays in which different enzymes could be deposited in turn. Enzyme deposition is generally described in Wilson, et al., U.S. Pat. No. 6,814,845; Ammam, et al., *Micro-biofuel cell powered by glucose/O$_2$ based on electro-deposition of enzyme, conducting polymer and redox mediators: Preparation, characterization and performance in human serum*, Biosens. Bioelectron. 25 1474-1480 (2010); Ammam et al., *AC-electrophoretic deposition of glucose oxidase*, Biosens. Bioelectron. 25 191-197 (2010); Ammam et al., *A study on electrodeposition of glucose oxidase from low conductivity solutions*, Electrochim. Acta 55(28) 9125-9131 (2010); Fransaer et al., WO 2010/040648A2, which are all incorporated by reference in their entirety.

Electrodeposition has been demonstrated to reproducibly prepare compact, active enzyme films about 500 nm thick. This is achieved by applying a positive potential of 0.8 V versus the reference electrode (e.g., the AgCl/Ag electrode). Thus negatively charged species move toward the positively charged conductor. A key issue is what triggers the deposition. It was demonstrated that because this deposition was carried out under conditions where the ionic species carrying the current is not primarily the enzyme, deposition was related to pH changes at the conductor surface. The disadvantage of this general approach is that in order to accomplish the deposition, high concentrations of enzyme are required. Some enzymes are quite expensive, so a process to make this process more efficient is clearly advantageous.

In the present invention, enzyme deposition was accomplished by lowering the ionic strength of the buffer in which the deposition is carried out and by immobilizing the enzyme on a nanoparticle with a high negative charge. This approach allows the pH of the solution to be maintained while increasing electrophoretic efficiency for nanoparticle deposition. The potential across the electrodes during electrodeposition is preferably from about 0.5 V to 1.2 V, and the ionic strength is preferably from about 0.0001 M to about 0.001 M, the pH is preferably about 7 to about 8, and the potential is preferably applied for from about 1 minute to about 30 minutes.

FIGS. 8, 12 and 13 demonstrated that it was possible to deposit enzyme within the substrate cavity to produce a biosensor which yields a linear response to the test system (covalently attached glucose oxidase nanoparticles and glucose solutions of varying concentration). It will also be noted that the response was higher when the ionic strength of the solution was lowered. This is because under these conditions a larger part of the total current is carried by the nanoparticles, thus supporting the electrophoretic process. In this example, glucose oxidase enzyme covalently attached to magnetic iron oxide nanoparticles was deposited at a pH of about 7.4 without any coating in about four minutes at two ionic strengths. Similar results were observed for lactate oxidase covalently attached to magnetic iron oxide nanoparticles, and choline oxidase covalently attached to magnetic iron oxide nanoparticles (FIG. 9). Similar results are also observed for D-amino acid oxidase, (S)-6-hydroxynicotine oxidase, alcohol oxidase, pyruvate oxidase, glutamate oxidase, acyl coenzyme A oxidase, glutathione sulfhydryl oxidase, glycerolphosphate oxidase, sarcosine oxidase, xanthine oxidase, oxalate oxidase, cholesterol oxidase, gamma-glutamyl-putrescine oxidase, histamine oxidase (diamine oxidase), nucleoside oxidase, L-lysine oxidase, L-aspartate oxidase, glycine oxidase, and galactose oxidase.

This invention also finds utility for nanoparticles that are non-magnetic. This was demonstrated by covalently attaching glucose oxidase to gold particles (50 nm in diameter) and then electrophoretically depositing these particles into a capillary substrate cavity. The resulting dose-response plot showed that the nanoparticles with covalently attached glucose oxidase was successfully delivered into the cavity and was capable of measuring exogenous glucose when added (FIG. 10).

This invention also finds utility for nanoparticles that are coated with a carbohydrate (magnetic iron oxide coated with dextran, FIG. 14) or a non-conducting polymer (magnetic iron oxide coated with carbon layers, FIG. 15). For the case of the coated nanoparticles, a reduction of the background current may be observed, and this reduction in some instances may be preferred.

In addition to the deposition of the enzyme, the biosensor 10 includes a permselective membrane to exclude endogenous interferences such as ascorbate and urate. This is accomplished by electropolymerizing the deposited enzyme layer with phenol, which will anchor the nanoparticles in place and, at the same time, provide the desired permselective properties. The enzyme layer is preferably kept as thin as possible in order to optimize the sensor response time. Although oxidation of water can clearly occur at the applied potential of 0.8 V, the forces driving the nanoparticle deposition are capable of expelling the oxygen formed. In addition to phenol, substituted phenols can also be used to anchor the nanoparticles in place and simultaneously provide permselective properties.

More specifically, as generally set forth in Wilson, et al., U.S. Pat. No. 6,814,845, which is incorporated by reference, a selected synthetic monomer is electropolymerized at the locale of the deposited enzyme so as to create a polymer layer which is intermingled with the enzyme. It is believed that the electropolymerization process causes the monomer to be oxidized at the surface of the electrode and encapsulates much of the enzyme. The thickness of the polymer layer 90 formed is self-limiting, i.e., because the polymer is non-conducting, it cannot conduct electrons to become, in effect, an extension of the electrode. This means that the film will stop forming when communication with the electrode is interrupted. The starting monomer for this step is selected with certain end properties in mind. Generally, the polymeric film should have a thickness and permeability consistent with the desired biosensor, but generally the polymeric layer should have a thickness of up to about 100 nm, and more preferably from about 10 to about 100 nm. Second, the polymer film should have well-defined and reproducible permeability characteristics with optimal permeability for the enzyme substrate while excluding electroactive interferants such as ascorbate, urate, and acetaminophen. The single most preferred monomer for use in the electropolymerization step is phenol which should be present in an aqueous buffered phenol solution at pH 7. However, other candidate monomers include substituted phenols. Preferred phenol monomers include 4-aminophenol, 1,4-dihydroxybenzene, 1,3-dihydroxybenzene, 1,2-dihydroxybenzene, 3-hydroxytyramine, 1,3,5-trihydroxybenzene, and 1,2,3-trihydroxybenzene. The electropolymerization should assist in anchoring the particles in the capillary substrate cavity.

In the present invention, it is preferable to deposit the nanoparticles on the surface of the electrode at constant current, rather than constant potential (a galvanostatic rather than a potentiostatic approach), although both approaches can be used. Using this galvanostatic approach the charge required for the deposit will be related to integral of the current with time (charge). The process will not be 100% current efficient since oxygen is evolved, but a constant part of the current will be attributable to the nanoparticle deposition.

FIG. 1d is a schematic showing exemplary enzyme-immobilized nanoparticles 200. The nanoparticles 200 include a nanoparticle core 210 which may be magnetic or non-magnetic and a coating 220 having an activated group 230 ($R_2$) for covalent attachment of the enzyme. Further other functional groups 240 ($R_1$) may be incorporated in order to tailor the overall charge (and zeta potential) of the nanoparticles 200. The nanoparticles are preferably from about 30 nm to about 200 nm in diameter, and are preferably in the range from about 30 nm to about 100 nm range, for example about 30 nm, 35 nm, 40 nm, 45 nm, 50 nm, 55 nm, 60 nm, 65 nm, or 70 nm in diameter.

In an exemplary embodiment, a nanoparticle core 210 is encapsulated with a coating 220 comprised of a functionalized or functionalizable non-conducting material. This material may be a linear or branched carbohydrate polymer. The carbohydrate coating can be neutral or charged depending on the required electrophoretic properties of the composite system. The coated particles are reacted with a metallophile, such as a trimethylsilane, to cap any remaining metal surface. The carbohydrate coating is subsequently modified with a linker of appropriate size (typically 2 to 10 carbon atoms in length), and with a reactive group to provide the biorecognition attachment point. A variety of different protein-compatible attachment chemistries are available by this strategy, including amines and carboxylates.

The magnetic nanoparticles 210 are preferably spherical and are typically fashioned from iron, such as those commercially available from MagQu Co., Ltd. (Taiwan), Ocean Nanotech and Nanoparte. However, other metals including nickel samarium-cobalt and rare earth metals (e.g., yttrium, neodymium, and samarium) and alloys thereof may be used in place of an iron core. Indeed, permanent magnets utilizing neodymium are known and may be used. While the nanoparticle core is presumed to be spherical, the ensuing discussion supports any realistic three-dimensional geometry. The spheres are of a size (typically from about 35 nm to about 200 nm in diameter) to support attachment of the biorecognition elements, while still providing a sufficient overall magnetic moment to allow for separation of the particles from reaction mixtures. By virtue of the core's magnetic properties, the ability to move the nanoparticles between reaction vessels enhances the manufacturability and reproducibility of the microbiosensor fabrication process. While cores based on iron are the most available, the present invention is applicable to variety of different magnetic core materials including nickel, cobalt, yttrium, neodymium, samarium. Combinations (e.g., alloys, composites, or mixtures/compositions) of the foregoing metals may also be used.

This invention also anticipates the use of non-magnetic nanoparticles 210. These are also preferably spherical and are typically fashioned from gold, silver, platinum, manganese, palladium, copper, zinc, ruthenium, rhodium, and/or cadmium. Combinations (e.g., alloys, composites, or mixtures/compositions) of the foregoing metals may also be used. While the nanoparticle core is presumed to be spherical, the ensuing discussion supports any realistic three-dimensional geometry. The spheres are of a size (typically from about 35 nm to about 200 nm in diameter) to support attachment of the biorecognition elements. While the non-magnetic nanoparticles will not facilitate the facile purification of the enzyme functionalized particles, and as such more traditional purification procedures must be employed, said non-magnetic nanoparticles will nonetheless be able to support the electrodeposition into a capillary substrate or other small cavity.

The coating 220 should preferably completely encase the magnetic core 210. This reduces noise and background current arising from the magnetic material. Further, the coating should prevent non-specific binding of proteinaceous materials, provide a convenient point of attachment of the biorecognition element and provide, when needed, a tunable molecular charge (e.g., negative) that can be used to modulate the electrophoretic properties of the sphere. Finally, the coating should be "biocompatible" in the sense that the coated magnetic nanoparticles do not elicit an immune response, yet resist biodegradation. Linear carbohydrate polymers based on random repeating subunits (e.g., dextrans, glycans, maltoses, heparin, heparan sulfate) and well-defined repeating subunits (e.g., celluloses, chitins, mucopolysaccharides, glycosaminoglycans such as hyaluronan, dermatan sulfate, keratan sulfate, chondroitin sulfate) are ideal materials to encapsulate the nanoparticle cores. See Lindahl, et al., *Glycosaminoglycans and their binding to biological macromolecules*, Rev. Biochem. 47 385-417 (1978); Hassell, et al., *Proteoglycan Core Protein Families*, Ann. Rev. Biochem. 55 539-567 (1986); Yeung, et al., *The Synthesis of Glycosaminoglycans* in Glycochemistry: Principles, Synthesis and Applications, Bertozzi, C. R.; Wang, G., Eds; Marcel Dekker: New York (1999); Yeung, et al., *Synthesis of Glycosaminoglycans*, J. Carbohydrate Chem. 21(7-9) 799-865 (2002), all of which are incorporated by reference.

By definition, linear carbohydrate polymers often consist of repeating units of mono, di, and trisaccharides where the repeating unit may be regular or random. The overall polymer may be neutral or charged. The geometry of the glycosidic linkage of linear carbohydrate polymers may be fixed (e.g. cellulose) or random (e.g. alginic acid). Linear carbohydrate polymers are grouped as families based on the repeating unit. Linear carbohydrate polymers that may find utility as nanoparticle coatings in this present invention include those taken from the group consisting of glycosaminoglycans (including hyaluronan, chondroitin, chondroitin sulfate, heparin, heparan sulfate, dermatan, dermatan sulfate, keratan, keratan sulfate), mucopolysaccharides, celluloses, pectins, glucomannans, galactomannans, agars, alginic acids, chitins, inulins, glucans, and amyloses. Branched carbohydrate polymers are more complex, and as appreciated by one skilled in the art, consist of multiple attachments that render the polymer non-linear. Branched carbohydrate polymers that may find utility as nanoparticle coatings in this present invention include those taken from the group consisting of amylopectins, xanthan gums, dextrans, glycogens, and arabinoxylans. For both the linear and branched carbohydrate polymers, said polymers may be chemically modified using standard procedures and protocols to modify one or more moieties on the polymer to facilitate attachment of the protein. These coatings may prove useful for both magnetic nanoparticles as well as non-magnetic nanoparticles.

Carbohydrate polymers that can encapsulate metal spheres are either naturally charged (as in the case of the mucopolysaccharides, heparin, heparin sulfates, glycosaminoglycans ("GAGs")) or may be made charged by oxidation of glycan core (e.g., dextrans, celluloses—see Yeung, 2002). These naturally occurring polymers are known to not elicit immune responses. Indeed, hyaluronan, heparin sulfate, and dermatan sulfate are used clinically with no observable immunogenesis. Further, carbohydrate polymers are utilized in medical devices to allow for biocompatibility and implantability.

It is anticipated that the carbohydrate coatings result in only an incremental change in the diameter of the nanospheres, and should add only from about 5 nm to about 20 nm, typically about 10 nm to the diameter of the magnetic core. Carbohydrate polymers can be neutral, or charged, and the net negative charge is chemically modifiable. For example, a controlled oxidation of free 6-OH with periodate will result in conversion to the corresponding uronic acid. This results in a net negative charge to the carbohydrate without compromising the fidelity of the polymer and can be used on any glycan with a free 6-OH, including dextran and cellulose. While the natural net negative charge of GAGs and mucopolysaccharides will assist in electrophoretic mobility of the particles, the highly polar, uncharged surface of other linear carbohydrate polymers may provide better overall properties. Various neutral and charged linear carbohydrate polymers can be tested, and for each polymer, the optimal dispersion can be tested. Exemplary polymers include chondroitin, heparin, and chitosan.

The choice of carbohydrate polymer utilized in the coating 220 dictates the type of linker 230 that is used to attach enzyme. For example, if the polymer is a GAG, adipic anhydride (a 6-carbon cyclic acid anhydride) can be used to attach the linker to the carbohydrate via an amide bond and reveal a second carboxylic acid moiety for protein attachment. In principle, any length cyclic anhydride may be employed. If the polymer has an uronic acid imbedded in the structure, the amino moiety of an epsilon amino acid can be attached to 6-COOH via standard amide forming chemistry, once again revealing a free carboxylate for attachment to the protein. A symmetrical diamine, such as hexa-diamine may also be employed, resulting in a free amine for attachment to the protein. The optimal length of the linker requires will require investigation once the core and the carbohydrate polymer have been chosen.

The size of the nanoparticle 210, the type of the carbohydrate polymer coating 220, and the linker 230 employed will, as a composite, directly dictate the density of protein biorecognition elements that can be achieved. For a nanoparticle core that is from about 30 nm to 50 nm in diameter and a carbohydrate coating that is from 5 nm to about 10 nm thick, from about 5 to about 15 (typically about 10) enzymatic molecules are expected to be attached to the nanoparticle.

The nanoparticles provide a standard platform for enzyme immobilization. It should be pointed out that one the reason for using magnetic particles is because this enables more careful control of the immobilization reaction conditions, including timing, a capability that is more difficult to achieve with non-magnetic particles are used.

Covalent attachment of the enzyme to the nanoparticle carboxylate surface may be accomplished using standard techniques. This will include attachment via primary amine, carboxylate, thiol, or aldehyde groups as examples.

This invention can also make use of non-covalent attachment of the enzyme to the nanoparticle via bioaffinity systems like the biotin-avidin system. Attachment of the enzyme to the nanoparticle utilizing bioaffinities is also possible using the avidin-biotin system or by the use of lectins. For example, using the avidin-biotin bioaffinity system, non-covalent immobilization of the enzyme might use a biotinylated enzyme which would attach to an avidin functionalized nanoparticle.

In all instances, the fidelity of the enzyme attachment to the nanoparticle can be verified prior to electrodeposition by assaying the beads against the natural substrate with a commercially available peroxide reporter system such as Amplex Red.

Surface charge was monitored by measurement of the zeta potential, which will typically be between about −20 mv to about −50 mV, with a preferred range of about −27 mV to about −45 mV. This parameter will be an indication of the particle electrophoretic mobility and also sufficiently high negative charge will also prevent or minimize aggregation as generally discussed in Pyell, *Characterization of nanoparticles by capillary electromigration separation techniques*, Electrophoresis 31(5) 814-831 (2010) and Tantra, et al., *Effect of nanoparticle concentration on zeta potential measurement results and reproducibility*, Particuology 8(3) 279-285 (2010), which are both incorporated by reference. The nanoparticles preferably carry large percentage of the current (e.g., typically more than 40%, 50%, 60%, 70%, or 80% or some range there between) during the electrodeposition process such that the ionic strength can be lowered towards zero, and is typically about 0.0001 M to about 0.001 M. This is demonstrated in FIGS. 12 and 13.

In another aspect of the present invention, the composite characteristics of the functionalized nanoparticles, including the zeta potential of the functionalized nanoparticle and the polydispersity of the sample as measured by its hydrodynamic radius, will play a role in determining the efficiency of the electrodeposition. The lack of electrodeposition efficiency can be compensated for by changing the ionic strength of the buffer, changing the charge carrying counter ion (e.g. changing the negative charged ion from chloride to nitrate), or by allowing the electrodeposition to occur for longer periods of time.

In the case of the magnetic iron-oxide nanoparticles functionalized with covalently attached glucose oxidase, the nanoparticles had a measured zeta potential of −33.6 mV, the non-magnetic glucose oxidase functionalized gold nanoparticles had a measured zeta potential of −36.0 mV, and the magnetic iron-oxide nanoparticles functionalized with choline oxidase had a measured zeta potential of −30.3 mV. In all instances, these nanoparticle systems had exceptional electrophoretic characteristics and were readily deposited into the capillary substrate cavity. The magnetic iron-oxide nanoparticles functionalized with glucose oxidase were essentially monodispersed in solution, but the non-magnetic glucose oxidase functionalized gold nanoparticles, and the magnetic iron-oxide nanoparticles functionalized with choline oxidase gave rise to multimodal polydispersities in solution.

In principle, the less aggregated (the lower polydispersity) of the nanoparticles, the more efficient the electrodeposition process. However, as above, this inefficiency may be compensated for experimentally. The polydispersity of a nanoparticle sample may be lowered by the inclusion of non-denaturing detergent or by the inclusion of one more additional proteins. The magnetic iron-oxide nanoparticles functionalized with lactate oxidase had a measured zeta potential of −47.5 mV and multimodal polydispersities in solution yet were still able to be electrophoretically deposited into the capillary substrate cavity, albeit at a slower rate and with less efficiency. Once inside the cavity, even poorly electrophoretically deposited nanoparticles are able to deliver enzyme proximal to the Pt working electrode and give rise to a discernible signal such as that seen for lactate oxidase response to lactate.

In the present invention, the biosensor and cannula are physically distinct. That is, the cannula will be implanted some time before the biosensor is inserted. After insertion, the biosensor is locked in place in the cannula. At that point, the electronic system must be connected to the working electrode (biosensor), reference electrode (integrated into the cannula or separate) and the biosensor shield. It is important that this connection is rigid to avoid motion artifacts and simple to use because the device may be used while the subject (such as a rat or mouse) may be awake. The electronics system should maintain a constant voltage between the working and reference electrode, drive the biosensor shield, and measure the extremely small currents produced by the biosensor. To further reduce noise, the electronics system is preferably located very near the biosensor, typically about 1 cm, 2 cm, or 3 cm from the biosensor. It is also preferable that the electronics system remain stationary with respect to the biosensor (e.g., it should not bounce), and all leakage paths in the overall system are extremely small (approximately $10^{12}$ ohms).

In a key aspect of the invention that is distinguishing relative to the prior art, the unique design of these biosensor imparts four essential performance properties: a. durable construction that can withstanding implantation (FIGS. 3, 4 and 5); b. significantly extended dynamic range without having to use mass transfer limiting membranes (FIGS. 8, 9, and 10); c. enhanced sensitivity due to efficient oxygen recycling (FIGS. 8, 12 and 13); d. limited oxygen consumption which makes high density arrays possible. Most biosensors only capture about 10% of the peroxide that is produced, the rest escapes into solution where it is destroyed. The geometry of the present device confines the enzyme in a very small cavity of about 5 pL or less in volume, made effectively even smaller than because the nanoparticles exclude solvent. The enzyme layer is also very thin (2-5 μm) and this promotes fast response. By making the recycling very efficient, probably in excess of 90%, both the linearity and the sensitivity are enhanced. Because the net consumption of oxygen is substantially reduced, this makes possible the construction of high density multi-analyte arrays (sensing elements closer to each other than 100 microns, see Yu, P. G., Wilson, G. S. "*An independently addressable microbiosensor array: What are the limits of sensing density?*", *Faraday Discuss.* 2000, 116, 305-317.) As shown in FIGS. 8, 12 and 13, the response of the glucose oxidase based biosensor can have a linear glucose response well in excess of approximately 15 mM, as predicted by a Michaelis constant of about 8-9 mM. It has been noted that oxygen recycling is a key parameter leading to an increase in the observed Michaelis constant and increased linearity of the biosensor response (see Csoregi, E. et al., *Design and Optimization of a Selective Subcutaneously Implantable Glucose Electrode Based on Wired Glucose Oxidase*, Anal. Chem. 1995, 67, 1240-1244.). This further suggests that oxygen recycling is occurring and that the recycling is efficient. Finally, this invention is general, and works with multiple enzymes (e.g. FIGS. 8, 9, 11 and 13) and with multiple types of nanoparticles that are uncoated (FIGS. 8, 9, 10, and 13) and coated (FIGS. 14 and 15).

In the present invention, the electrodeposition of the nanoparticles into a defined space, herein defined by the cavity of the capillary substrate, is general. The process in not limited by the enzyme as multiple enzymes were successfully deposited. The process is also not limited by the nanoparticle itself, and works equally as well with magnetic nanoparticles and non-magnetic nanoparticles. This invention is anticipated to work equally as well with any enzyme that can be attached to the nanoparticle. Furthermore, this invention is anticipated to work equally as well for any nanoparticle that is capable of electrophoretic movement. In addition, a distinguishing feature of this invention is that the make-up of the system promotes oxygen recycling in some instances—a feature of biosensor design and development that has heretofore not been attainable.

The present invention also anticipates extending the invention from a single capillary to multiple capillaries pulled together. State-of-the-art capillary pullers are able to simultaneously pull multiple capillaries together into a single unit where the individual capillaries are touching at the tips. Thus, multiple capillary substrates may be fabricated into an array such that each cavity therein may contain a different enzyme and each cavity therein may be individually and independently addressable. The present invention uses electrophoretic deposition to deliver a very small amount of enzyme to an electrochemically addressable array element. Each capillary substrate would be individually addressable, and consequently, this technique permits the development of sensor arrays in which different enzymes could be deposited in turn. The resulting biosensor array would allow for the monitoring of the concentration or concentration change or flux of multiple analytes simultaneously within the same in vivo region. Thus, glucose, glutamate, and lactate could all be monitored simultaneously in the same in vivo region. The ability to pull multiple capillaries together into a single unit would also permit the inclusion of one or more an integrated microinjection ports for analyte and drug delivery protocols. An example of such a unit is shown in FIG. 11, where three of the capillaries would be fashioned into capillary substrates and the fourth capillary would be used for drug delivery.

In another aspect of the invention, the implantable cannula with an integrated reference electrode, while a component of this present invention, may find utility in other applications and for other biosensors beyond those described herein. In this invention, the integrated reference electrode would provide for an electrical connection to an external electrical circuit. Any modality known to one skilled in the art may be used, and preferred modalities that minimize noise in the system can include coaxial and simple twisted pair electrical connections This type of cannula system can be made to accommodate any size biosensor that is implantable including those fashioned from multiple capillary substrates, Pt wire, Pt/Ir wire, carbon fiber, metal wire, metal alloy wire and ceramics. In many instances the biosensors; are sheathed in at least one layer of non-conducting material, such as glass, silica, Teflon, para-aramid polymer, carbon nanotubes, and graphene. In this aspect of the invention, the reference electrode is taken from the group comprising silver, gold, platinum, iridium, copper, iron, stainless steel, and combinations (e.g., alloys, composites, and/or mixtures/compositions) thereof. The cannula shaft may be comprised of layers of conducting and non-conducting material. Alternatively, the shaft may be composed of silver, gold, platinum, iridium, copper, iron, stainless steel, and combinations (e.g., alloys, composites, and/or mixtures/compositions) thereof.

In another aspect of the invention, the shaft is composed of at least two layers, wherein the inner-most layer is composed of non-conducting material and the outer-most layer is composed of conducting material, said conducting material acting as said reference electrode. In yet another aspect of the invention, said shaft is composed of at least three layers, wherein the inner-most layer is composed of non-conducting material and the outer-most layer is composed of conducting material, said conducting material acting as said reference electrode. The length of the shaft can range from about 0.1 mm to about 25 cm, but is in principle not limiting to the invention. The diameter of the shaft can range from 1 µm to about 5 mm and is not limiting to the invention.

In another aspect of the invention, the cannula may be composed of an integrated reference electrode and could be made to service any diameter biosensor including ranges from about 1 µm to about 5 mm. In accordance with other aspects of this invention, a cannula with an integrated reference electrode may also function as a Faraday cage and reduce electrical noise in the system. This aspect of the invention is completely compatible with any material used to construct external reference electrodes, and includes silver, gold, platinum, iridium, copper, iron, stainless steel, and combinations (e.g., alloys, composites, and/or mixtures/compositions) thereof, and includes any treatment necessary to convert the metal into a proper functioning reference electrode. An example would be the treatment of a silver layer with silver chloride using procedures known to one skilled in the art to provide an Ag/AgCl reference.

From the foregoing it will be seen that this invention is one well adapted to attain all ends and objectives hereinabove set forth, together with the other advantages which are obvious and which are inherent to the invention. Since many possible embodiments may be made of the invention without departing from the scope thereof, it is to be understood that all matters herein set forth or shown in the accompanying drawings are to be interpreted as illustrative, and not in a limiting sense. While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

Experimental Procedures

Capillary Preparation

A 25 µm diameter platinum wire (California Fine Wire) was epoxied to a 30 µm diameter carbon fiber (Specialty Materials, Lowell, Mass.) and then, using the carbon fiber as a guide wire, the platinum was introduced into a borosilicate capillary tube (length=4 in., inner diameter=0.58 mm, Catalog #1B100-4, World Precision Instruments, Sarasota, Fla.). The platinum wire was disconnected from the carbon fiber and arranged within the capillary tube such that the platinum wire extended 1.5 inches from both sides of the capillary tube.

Capillary Pulling

Capillaries containing the 25 µm platinum wire were then individually pulled to form a tapered sheath around the 25 µm platinum wire. All capillaries were pulled using a Narishige PE-21 Capillary puller (settings; heater=53.4, main-magnet=35.6; sub-magnet=4.4). Two tapered capillary electrodes were produced from each capillary tube pulled.

Capillary Finishing

Each tapered capillary electrode was inspected under a light microscope and trimmed using surgical scissors such that the platinum wire was cut nearly flush with the end of the pulled capillary sheath. The platinum wire was then fixed into place within the tapered capillary by dipping the tip in UV-activated epoxy (Type:Elc-4481, Part#82468, Batch#110824, from Electro-Lite Corp) for approximately 1 minute to allow capillary action to draw the epoxy within the tapered capillary. The exterior of the tip was then rinsed in acetone prior to exposure to the UV light source for about 15 seconds (LED-200, Electro-Lite Corp).

Capillary Connection

A connector was fashioned to the opposite (non-tapered) end of the pulled capillary by filling the capillary tube with colloidal silver (Ted Pella Inc.) with the 25 µm platinum wire extending out of the capillary. The male end of a small metal connector pin (Digi-Key, part #9407-015011127-100-ND) was then coated with colloidal silver and inserted into the colloidal silver filled capillary tube. The 25 µm platinum wire was then cut flush to the male connector pin and the male pin was secured in place with UV-activated epoxy (Type:Elc-4481, Part#82468, Batch#110824, from Electro-Lite Corp) using an UV light source for about 15 seconds (LED-200, Electro-Lite Corp).

Capillary Electrode Testing

Each capillary electrode was tested in vitro prior to etching. Electrodes were placed in a beaker of 20 mL of 100 mM phosphate buffered saline and connected to a Pinnacle Technology Model 8102 Potentiostat. A bias of 0.6 V with respect to an Ag/AgCl reference electrode was applied to the capillary electrode. Hydrogen peroxide (Sigma Aldrich) was then added into the testing buffer in multiple aliquots (Final Concentrations: 10 µM, 10 µM, 20 µM, 20 µM, 100 µM). Only electrodes that showed clear responses to hydrogen peroxide were kept for further use.

Electrode Etching

Etching was accomplished by immersing each capillary electrode in a 4M NaCN/1M KOH solution. A secondary platinum electrode was also immersed in the solution to act as a counter electrode. The counter and capillary electrode were then connected to a waveform generator (Agilent 33210A) and a square wave (4.0 Vpp, 250 Hz) was applied to the two electrodes for about 0.5 seconds to about 5 seconds. The applied waveform was verified in series with a Tektronix TDS 2014 oscilloscope. Capillary electrodes were removed from the reaction vessel, rinsed with 0.1M KOH and then sonicated in nanopure water for 5 minutes. Capillary substrates were then stored immersed in buffer comprised of 10 mM $NaH_2PO_4$ & 1 mM NaCl (pH 7.2).

Particle Deposition

Capillary substrates were lowered into a reaction vessel filled with the enzyme attached nanoparticle solution and connected in circuit with a platinum counter electrode and Ag/AgCl reference electrode. A CH Instruments 814c Electrochemical Detector (in amperometric i/t curve mode) was used to apply a 1.0 V bias to the capillary electrode for up to sixteen minutes.

Biosensor Testing

Testing of each electrode was carried out on a CH Instruments 6205c Electrochemical Detector in 100 mM phosphate buffered saline. A 0.6 V bias was applied to each capillary electrode and allowed time to reach a stable baseline level. The analyte of interest was then added to the testing vessel in 5 mM (final concentration) aliquots up to at least 15 mM.

At the completion of the test, electrodes were stored in buffer comprised of 10 mM $NaH_2PO_4$ & 1 mM NaCl (pH 7.2).

Nanoparticle Functionalization

Nanoparticles were functionalized according to the methods of Wu et al. (Analytical Chemistry, 2010, 82, 1427). Briefly, 0.2 mL of nanoparticles were placed in a 1.5 mL vial to which was sequentially added 0.3 mL of 10 mM $NaH_2PO_4$ buffer (pH 7.4) and 0.5 mL of EDC/NHS solution. The mixture was allowed to incubate on ice for 30 minutes, after which 0.5 mL of glucose oxidase solution was added. The resulting mixture was allowed to incubate overnight at 4° C. with continuous gentle mixing. Subsequently, ethanol amine was added (10 μL) and the resulting mixture allowed to further incubate at 4° C. for 30 minutes. The nanoparticles in the resulting mixtures were washed and processed according to the nature of the nanoparticle.

For magnetic nanoparticles, a permanent magnet was placed in a filled ice bucket, and the vial containing the mixture was placed on the ice covered surface of the magnet. The supernantant was removed and the beads washed five times with 10 mM $NaH_2PO_4$ that was allowed to sit atop the nanoparticles for 5-10 minutes per wash. The nanoparticles were resuspended in 10 mM $NaH_2PO_4$ buffer for storage prior to electrodeposition.

For non-magnetic nanoparticles, the mixture was centrifuged at 4000 RPM for 10-15 minutes and the supernatant removed. The nanoparticles were resuspended in 1 mL of buffer, and recentrifuged for 10 minutes at 4000 RPM and this procedure was repeated at least five times. After the washing was complete, the particles were resuspended in 10 mM $NaH_2PO_4$ buffer for storage prior to electrodeposition.

EDC/NHS solution was made by combining 0.5 mL of a 10 mM $NaH_2PO_4$ buffer, 2 mg of N-(3-dimethylaminopropyl)-N'-ethylcarbodiimide hydrochloride (EDC) and 1 mg of N-hydroxysuccinimide (NHS).

Iron oxide nanoparticles were purchased from Ocean Nanotech (#SHP-50-50) with an average diameter of 50 nm and from MagQu Co., Ltd. (Taiwan). Gold nanoparticles were purchased from Nanoparte (#20-PC-50-50) with an average diameter of 50 nm.

We claim:

1. A tissue implantable biosensor system comprising:
   a capillary substrate;
   a conductive electrode within said capillary substrate, said capillary substrate having a cavity at one end;
   a plurality of nanoparticles having an enzyme immobilized thereon deposited in said cavity; and
   a reference electrode.

2. The tissue implantable biosensor system of claim 1, wherein said capillary substrate has an exterior surface coated with a reinforcing material coating.

3. The tissue implantable biosensor system of claim 2, wherein said reinforcing material coating selected from the group consisting of a para-aramid polymer coating, carbon nanotube coating, and grapheme coating.

4. The tissue implantable biosensor system of claim 3, wherein said reinforcing material forms an electric shield around said capillary substrate which reduces electrical noise and dielectric absorption effects in said system.

5. The tissue implantable biosensor system of claim 2, wherein said reinforcing material coating has a thickness from about 2 nm to about 100 nm.

6. The tissue implantable biosensor system of claim 2, wherein said reinforcing material coating has an overlying insulating layer.

7. The tissue implantable biosensor system of claim 1, wherein said conductive electrode comprises a metal or metal alloy wire which is sealed in the capillary substrate and etched to a depth to form said cavity.

8. The tissue implantable biosensor system of claim 7, wherein a resin seals said wire in said capillary substrate.

9. The tissue implantable biosensor system of claim 1, wherein said capillary substrate is housed in a cannula.

10. The tissue implantable biosensor system of claim 9, wherein said reference electrode is integrated in said cannula.

11. The tissue implantable biosensor system of claim 10, wherein said cannula is tapered.

12. The tissue implantable biosensor system of claim 10, wherein a conducting layer is formed on said cannula, said conducting layer forming an electric shield around said biosensor which reduces electrical noise and dielectric absorption effects in said system.

13. The tissue implantable biosensor system of claim 12, wherein an insulating layer overlies said conducting layer.

14. The tissue implantable biosensor system of claim 1, wherein said nanoparticles comprise a nanoparticle core and a coating on said nanoparticle core, said coating comprising an activated group for covalent attachment of said enzyme to said nanoparticle core.

15. The tissue implantable biosensor system of claim 14, wherein said nanoparticle core comprises a metal, a metal alloy, or a combination thereof.

16. The tissue implantable biosensor system of claim 14, wherein said nanoparticle core is magnetic.

17. The tissue implantable biosensor system of claim 16, wherein said nanoparticle core is selected from the group consisting of iron, nickel, cobalt, yttrium, neodymium, samarium, and combinations thereof.

18. The tissue implantable biosensor system of claim 14, wherein said nanoparticle core is non-magnetic.

19. The tissue implantable biosensor system of claim 18, wherein said nanoparticle core is selected from group consisting of gold, silver, platinum, manganese, palladium, copper, zinc, ruthenium, rhodium, cadmium, stainless steel, iridium, and combinations thereof.

20. The tissue implantable biosensor system of claim 14, wherein said coating is non-conducting.

21. The tissue implantable biosensor system of claim 14, wherein said coating comprises a carbohydrate polymer.

22. The tissue implantable biosensor system of claim 14, wherein said coating comprises a linear carbohydrate polymer.

23. The tissue implantable biosensor system of claim 14, wherein said coating comprises a polymer selected from the group consisting of glycosaminoglycans (including hyaluronan, chondroitin, chondroitin sulfate, heparin, heparan sulfate, dermatan, dermatan sulfate, keratan, keratan sulfate), mucopolysaccharides, celluloses, pectins, glucomannans, galactomannans, agars, alginic acids, chitins, inulins, glucans amylases, amylopectins, xanthan gums, dextrans, glycogens, arabinoxylans, and combinations thereof.

24. The tissue implantable biosensor system of claim 14, wherein said nanoparticle core is completely coated with said coating.

25. The tissue implantable biosensor system of claim 14, wherein said coating is from about 5 nm to about 10 nm thick.

26. The tissue implantable biosensor system of claim 14, wherein said enzyme is attached to said coating via a group selected from the group consisting of primary amines, carboxylates, thiols, aldehyde moieties, and non-covalently attachments using bioaffinities.

27. The tissue implantable biosensor system of claim 14, wherein said enzyme is an oxidase enzyme selected from the group consisting of malate oxidase, hexose oxidase, aryl-alcohol oxidase, L-gulonolactone oxidase, pyranose oxidase, L-sorbose oxidase, pyridoxine 4-oxidase (S)-2-hydroxy-acid oxidase, ecdysone oxidase, secondary-alcohol oxidase, 4-hydroxymandelate oxidase, long-chain-alcohol oxidase, thiamine oxidase, hydroxyphytanate oxidase, N-acylhexosamine oxidase, polyvinyl-alcohol oxidase, D-arabinono-1,4-lactone oxidase, vanillyl-alcohol oxidase, D-mannitol oxidase, alditol oxidase, choline dehydrogenase, gluconate 2-dehydrogenase, glucooligosaccharide oxidase, alcohol dehydrogenase, cellobiose dehydrogenase, aldehyde oxidase, glyoxylate oxidase, indole-3-acetaldehyde oxidase, aryl-aldehyde oxidase, retinal oxidase, abscisic-aldehyde oxidase, aldehyde ferredoxin oxidoreductase, indolepyruvate ferredoxin oxidoreductase, aldehyde dehydrogenase, dihydroorotate oxidase, dihydrouracil oxidase, tetrahydroberberine oxidase, tryptophan alpha,beta-oxidase, L-galactonolactone oxidase, acyl-CoA dehydrogenase, isoquinoline 1-oxidoreductase, quinaldate 4-oxidoreductase, D-aspartate oxidase, L-amino-acid oxidase, monoamine oxidase, pyridoxal 5'-phosphate synthase, D-glutamate oxidase, ethanolamine oxidase, putrescine oxidase, cyclohexylamine oxidase, protein-lysine 6-oxidase, D-glutamate(D-aspartate) oxidase, L-lysine 6-oxidase, primary-amine oxidase, 7-chloro-L-tryptophan oxidase, N-methyl-L-amino-acid oxidase, non-specific polyamine oxidase, N8-acetylspermidine oxidase (propane-1,3-diamine-forming), N6-methyl-lysine oxidase, polyamine oxidase (propane-1,3-diamine-forming), N1-acetylpolyamine oxidase, spermine oxidase, L-pipecolate oxidase, dimethylglycine oxidase, polyamine oxidase, E-dihydrobenzophenanthridine oxidase, NAD(P)H oxidase, urate oxidase, aci-nitropropanoate oxidase, sulfite oxidase, methanethiol oxidase, prenylcysteine oxidase, L-ascorbate oxidase, 3-hydroxyanthranilate oxidase, rifamycin-B oxidase, superoxide dismutase, reticuline oxidase, lactate oxidase, D-amino acid oxidase, (S)-6-hydroxynicotine oxidase, (R)-6-hydroxynicotine oxidase, alcohol oxidase, pyruvate oxidase, glucose oxidase, glutamate oxidase, acyl coenzyme A oxidase, choline oxidase, glutathione sulfhydryl oxidase, glycerolphosphate oxidase, sarcosine oxidase, xanthine oxidase, oxalate oxidase, cholesterol oxidase, gamma-glutamyl-putrescine oxidase, GABA oxidase, histamine oxidase, diamine oxidase, nucleoside oxidase, L-lysine oxidase, L-aspartate oxidase, glycine oxidase, and galactose oxidase.

28. The tissue implantable biosensor system of claim 14, wherein said enzyme is an oxidase enzyme selected from the group consisting of lactate oxidase, D-amino acid oxidase, (S)-6-hydroxynicotine oxidase, (R)-6-hydroxynicotine oxidase, alcohol oxidase, pyruvate oxidase, glucose oxidase, glutamate oxidase, acyl coenzyme A oxidase, choline oxidase, glutathione sulfhydryl oxidase, glycerolphosphate oxidase, sarcosine oxidase, xanthine oxidase, oxalate oxidase, cholesterol oxidase, gamma-glutamyl-putrescence oxidase, GABA oxidase, histamine oxidase, diamine oxidase, nucleoside oxidase, L-lysine oxidase, L-aspartate oxidase, glycine oxidase, and galactose oxidase.

29. The tissue implantable biosensor system of claim 1, wherein said nanoparticles are from about 30 am to about 200 nm in diameter.

30. The tissue implantable biosensor system of claim 1, wherein the number of capillary substrates is from about one to about eight.

* * * * *